United States Patent
Wang et al.

(10) Patent No.: US 10,431,361 B2
(45) Date of Patent: Oct. 1, 2019

(54) APPARATUSES AND METHODS FOR CANCELLATION OF INHOMOGENOUS MAGNETIC FIELDS INDUCED BY NON-BIOLOGICAL MATERIALS WITHIN A PATIENT'S MOUTH DURING MAGNETIC RESONANCE IMAGING

(71) Applicant: THE BOARD OF REGENTS OF THE UNIVERSITY OF TEXAS SYSTEM, Austin, TX (US)

(72) Inventors: Zhiyue J. Wang, Dallas, TX (US); Yong Jong Park, Dallas, TX (US); Nancy K. Rollins, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 572 days.

(21) Appl. No.: 15/134,211

(22) Filed: Apr. 20, 2016

(65) Prior Publication Data
US 2016/0231401 A1    Aug. 11, 2016

Related U.S. Application Data

(63) Continuation-in-part of application No. 14/153,516, filed on Jan. 13, 2014, now Pat. No. 9,368,265.

(51) Int. Cl.
*H01F 7/02* (2006.01)
*G01R 33/3873* (2006.01)
(Continued)

(52) U.S. Cl.
CPC ......... *H01F 7/0273* (2013.01); *A61B 5/0042* (2013.01); *A61B 5/055* (2013.01);
(Continued)

(58) Field of Classification Search
CPC ........ A61F 5/56; A61F 5/566; Y10S 602/902; H01F 7/0278; H01F 7/0273;
(Continued)

(56) References Cited

U.S. PATENT DOCUMENTS 5,143,086 A * 9/1992 Duret ................... A61B 5/1127
600/590
6,968,982 B1 11/2005 Burns et al. ............... 222/321.9
(Continued)

OTHER PUBLICATIONS

ACR: Phantom Test Guidance. Available from: http://www.acr.org/~/media/ACR/Documents/Accreditation/MRI/LargePhantomGuidance.pdf, accessed Apr. 15, 2014.
(Continued)

*Primary Examiner* — Mohamad A Musleh
(74) *Attorney, Agent, or Firm* — Norton Rose Fulbright US LLP

(57) ABSTRACT

This disclosure includes magnetic field correction devices and methods for using the same. In particular, some magnetic field corrections devices include an arch-shaped body configured to be worn outside of a user's mouth such that the arch-shaped body follows a contour of the user's face; and where the arch-shaped body comprises one or more sidewalls configured to be coupled to a plurality of members comprising magnetically permeable material. Other embodiments employ a forehead support, frame, and one or more straps coupled to an arch-shaped body. Other embodiments employ a hybrid of intraoral and external embodiments.

26 Claims, 12 Drawing Sheets

(51) Int. Cl.
  *A61B 5/055*  (2006.01)
  *G01R 33/28*  (2006.01)
  *A61C 7/12*  (2006.01)
  *A61B 5/00*  (2006.01)
  *A61B 5/026*  (2006.01)
  *G01R 33/565*  (2006.01)

(52) U.S. Cl.
  CPC ............ *A61B 5/4547* (2013.01); *A61C 7/125* (2013.01); *G01R 33/285* (2013.01); *G01R 33/3873* (2013.01); *A61B 5/0263* (2013.01); *A61B 2576/026* (2013.01); *G01R 33/56536* (2013.01)

(58) Field of Classification Search
  CPC .............. G01R 33/3873; G01R 33/285; G01R 33/56536; A61B 5/0042; A61B 5/055; A61B 5/4547; A61B 5/0263; A61B 2576/026; A61C 7/125
  See application file for complete search history.

(56) References Cited

U.S. PATENT DOCUMENTS

| | | | | |
|---|---|---|---|---|
| 2007/0137654 | A1* | 6/2007 | Paraschac | A61F 5/56 128/848 |
| 2007/0137655 | A1* | 6/2007 | Paraschac | A61F 5/56 128/848 |
| 2007/0144533 | A1* | 6/2007 | Nelson | A61F 2/00 128/848 |
| 2008/0199824 | A1* | 8/2008 | Hargadon | A61F 5/566 433/6 |
| 2013/0137057 | A1* | 5/2013 | Schmitt | A61C 9/0006 433/29 |
| 2016/0262856 | A1* | 9/2016 | Atiya | A61C 9/006 |

OTHER PUBLICATIONS

Adam CJ, Askin GN, and Pearcy MJ: Gravity-induced torque and intravertebral rotation in idiopathic scoliosis. Spine (Phila Pa 1976) 2008; 33(2): p. E30-7. PMID: 18197088.
Bagheri MH, Hosseini MM, Emami MJ, and Foroughi AA: Metallic artifact in MRI after removal of orthopedic implants. Eur J Radiol 2012; 81(3): p. 584-90. PMID: 21146947.
Bateman LM, Latchaw R, and Seyal M: Dental hardware complicating diagnosis in refractory gelastic epilepsy secondary to hypothalamic hamartoma. Clin EEG Neurosci 2010; 41(3): p. 151-4. PMID: 20722350.
Blankenstein FH, Truong B, Thomas A, Schroder RJ, and Naumann M: Signal loss in magnetic resonance imaging caused by intraoral anchored dental magnetic materials. Rofo 2006; 178(8): p. 787-93. PMID: 16862505.
Boeckler AF, Morton D, Ehring C, and Setz JM: Mechanical properties of magnetic attachments for removable prostheses on teeth and implants. J Prosthodont 2008; 17(8): p. 608-15. PMID: 18761583.
Bondemark L, Kurol J, and Wennberg A: Orthodontic rare earth magnets—in vitro assessment of cytotoxicity. Br J Orthod 1994; 21(4): p. 335-41. PMID: 7857892.
Bondemark L: Orthodontic magnets. A study of force and field pattern, biocompatibility and clinical effects. Swed Dent J Suppl 1994; 99: p. 1-148. PMID: 7801229.
Buckwalter KA, Lin C, and Ford JM: Managing postoperative artifacts on computed tomography and magnetic resonance imaging. Semin Musculoskelet Radiol 2011; 15(4): p. 309-19. PMID: 21928156.
Cox RJ, Kau CH, and Rasche V: Three-dimensional ultrashort echo magnetic resonance imaging of orthodontic appliances in the natural dentition. Am J Orthod Dentofacial Orthop 2012; 142(4): p. 552-61. PMID: 22999679.

Cullity BD and Graham CD: Introduction to Magnetic Materials. 2nd ed. 2009: Wiley.
David FH, Grierson J, and Lamb CR: Effects of surgical implants on high-field magnetic resonance images of the normal canine stifle. Vet Radiol Ultrasound 2012; 53(3): p. 280-8. PMID: 22372640.
Donohue VE, McDonald F, and Evans R: In vitro cytotoxicity testing of neodymium-iron-boron magnets. J Appl Biomater 1995; 6(1): p. 69-74. PMID: 7703540.
Elison JM, Leggitt VL, Thomson M, Oyoyo U, and Wycliffe ND: Influence of common orthodontic appliances on the diagnostic quality of cranial magnetic resonance images. Am J Orthod Dentofacial Orthop 2008; 134(4): p. 563-72. PMID: 18929275.
Ernstberger T and Heidrich G: Postfusion magnetic resonance imaging artifacts caused by a titanium, cobalt-chromium-molybdenum, and carbon intervertebral disc spacer. J Spinal Disord Tech 2007; 20(2): p. 154-9. PMID: 17414986.
Ernstberger T, Buchhorn G, and Heidrich G: Artifacts in spine magnetic resonance imaging due to different intervertebral test spacers: an in vitro evaluation of magnesium versus titanium and carbon-fiber-reinforced polymers as biomaterials. Neuroradiology 2009; 51(8): p. 525-9. PMCID: PMC3085728.
Ernstberger T, Buchhorn G, and Heidrich G: Magnetic resonance imaging evaluation of intervertebral test spacers: an experimental comparison of magnesium versus titanium and carbon fiber reinforced polymers as biomaterials. Ir J Med Sci 2010; 179(1): p. 107-11. PMCID: PMC3128752.
Ernstberger T, Buchhorn G, Baums MH, and Heidrich G: In-vitro MRI detectability of interbody test spacers made of carbon fibre-reinforced polymers, titanium and titanium-coated carbon fibre-reinforced polymers. Acta Orthop Belg 2007; 73(2): p. 244-9. PMID: 17515239.
Ernstberger T, Heidrich G, and Buchhorn G: Postimplantation MRI with cylindric and cubic intervertebral test implants: evaluation of implant shape, material, and volume in MRI artifacting—an in vitro study. Spine J 2007; 7(3): p. 353-9, PMID: 17482121.
Ernstberger T, Heidrich G, Bruening T, Krefft S, Buchhorn G, and Klinger HM: The interobserver-validated relevance of intervertebral spacer materials in MRI artifacting. Eur Spine J 2007; 16(2): p. 179-85. PMCID: PMC2200688.
Ernstberger T, Heidrich G, Dullin C, Buchhorn G, and Grabbe E: Preclinical evaluation by flat-panel detector-based volumetric CT versus MRI of intervertebral spacers implanted in a porcine model. Spine J 2007; 7(3): p. 360-7. PMID: 17482122.
Ernstberger T, Heidrich G, Schultz W, and Grabbe E: Implant detectibility of intervertebral disc spacers in post fusion MRI: evaluation of the MRI scan quality by using a scoring system—an in vitro study. Neuroradiology 2007; 49(2): p. 103-9. PMID: 17086407.
Fache JS, Price C, Hawbolt EB, and Li DK: MR imaging artifacts produced by dental materials. AJNR Am J Neuroradiol 1987; 8(5): p. 837-40. PMID: 3118677.
Fellner C, Behr M, Fellner F, Held P, Handel G, and Feuerbach S: Artifacts in MR imaging of the temporomandibular joint caused by dental alloys: a phantom model study at T1.5. Rofo 1997; 166(5): p. 421-8. PMID: 9198515.
Gholipour A, Kehtarnavaz N, Scherrer B, and Warfield SK: On the accuracy of unwarping techniques for the correction of susceptibility-induced geometric distortion in magnetic resonance Echo-planar images. Conf Proc IEEE Eng Med Biol Soc 2011; 2011: p. 6997-7000. PMID: 22255949.
Hargreaves BA, Worters PW, Pauly KB, Pauly JM, Koch KM, and Gold GE: Metal-induced artifacts in MRI. AJR Am J Roentgenol 2011; 197(3): p. 547-55. PMID: 21862795.
Hashemi RH, Bradley WG, and Lisanti CJ: MRI: The Basics. 3rd ed. 2010: Lippincott Williams & Wilkins.
Hecht S, Adams WH, Narak J, and Thomas WB: Magnetic resonance imaging susceptibility artifacts due to metallic foreign bodies. Vet Radiol Ultrasound 2011; 52(4): p. 409-14. PMID: 21382122.
Heyse TJ, Chong le R, Davis J, Boettner F, Haas SB, and Potter HG: MRI analysis of the component-bone interface after TKA. Knee 2012; 19(4): p. 290-4. PMID: 21741843.
Hinshaw DB, Jr., Holshouser BA, Engstrom HI, Tjan AH, Christiansen EL, and Catelli WF: Dental material artifacts on MR images. Radiology 1988; 166(3): p. 777-9. PMID: 3340777.

(56) References Cited

OTHER PUBLICATIONS

Immel E and Melzer A: Improvement of the MR imaging behavior of vascular implants. Minim Invasive Ther Allied Technol 2006; 15(2): p. 85-92. PMID: 16754191

Jin Z, Xia L, and Du YP: Reduction of artifacts in susceptibility-weighted MR venography of the brain. J Magn Reson Imaging 2008; 28(2): p. 327-33. PMCID: PMC2782378.

Kagetsu NJ and Litt AW: Important considerations in measurement of attractive force on metallic implants in MR imagers. Radiology 1991; 179(2): p. 505-8. PMID: 2014301.

Klinke T, Daboul A, Maron J, Gredes T, Puls R, Jaghsi A, and Biffar R: Artifacts in magnetic resonance imaging and computed tomography caused by dental materials. PLoS One 2012; 7(2): p. e31766. PMCID: PMC3285178.

Koch KM, Brau AC, Chen W, Gold GE, Hargreaves BA, Koff M, McKinnon GC, Potter HG, and King KF: Imaging near metal with a MAVRIC-SEMAC hybrid. Magn Reson Med 2011; 65(1): p. 71-82. PMID: 20981709.

Kolind SH, MacKay AL, Munk PL, and Xiang QS: Quantitative evaluation of metal artifact reduction techniques. J Magn Reson Imaging 2004; 20(3): p. 487-95. PMID: 15332257.

Laakman RW, Kaufman B, Han JS, Nelson AD, Clampitt M, O'Block AM, Haaga JR, and Alfidi RJ: MR imaging in patients with with metallic implants. Radiology 1985; 157(3): p. 711-4. PMID: 4059558.

Lee YH, Lim D, Kim E, Kim S, Song HT, and Suh JS: Usefulness of slice encoding for metal artifact correction (SEMAC) for reducing metallic artifacts in 3-T MRI. Magn Reson Imaging 2013; [Epub ahead of print]. PMID: 23290476.

Lopic N, Jelen A, Vrtnik S, Jaglicic Z, Wencka M, Starc R, Blinc A, and Dolinsek J: Quantitative determination of magnetic force on a coronary stent in MRI. J. Magn Reson Imaging 2013; 37(2): p. 391-7. PMID: 23125054.

Mirvis SE, Geisler F, Joslyn JN, and Zrebeet H: Use of titanium wire in cervical spine fixation as a means to reduce MRI artifacts. AJNR Am J Neuroradiol 1988; 9(6): p. 1229-31. PMID: 3143247.

Morelli J, Porter D, Ai F, Gerdes C, Saettele M, Feiweier T, Padua A, Dix J, Marra M, Rangaswamy R, and Runge V: Clinical evaluation of single-shot and readout-segmented diffusion-weighted imaging in stroke patients at 3 T. Acta Radiol 2013; [Epub ahead of print]. PMID: 23319722.

New, et al., "Potential hazards and artifacts of ferromagnetic and nonferromagnetic surgical and dental materials and devices in nuclear magnetic resonance imaging." Radiology 147(1): 139-48, 1983.

Olsen RV, Munk PL, Lee MJ, Janzen DL, MacKay AL, Xiang QS, and Masri B: Metal artifact reduction sequence: early clinical applications. Radiographics 2000; 20(3): p. 699-712. PMID: 10835123.

Palinkas M, Nassar MS, Cecilio FA, Siessere S, Semprini M, Machado-de-Sousa JP, Hallak JE, and Regalo SC: Age and gender influuence on maximal bite force and masticatory muscles thickness. Arch Oral Biol 2010; 55(10): p. 797-802. PMID: 20667521.

Pauchard Y, Smith MR, and Mintchev MP: Improving geometric accuracy in the presence of susceptibility difference artifacts produced by metallic implants in magnetic resonance imaging. IEEE Trans Med Imaging 2005; 24(10): p. 1387-99. PMID: 16229424.

Phelan A, Petocz P, Walsh W, and Darendeliler MA: The force-distance properties of attracting magnetic attachments for tooth movement in combination with clear sequential aligners. Aust Orthod J 2012; 28(2): p. 159-69. PMID: 23304964.

Ramos-Cabrer P, van Duynhoven JP, Van der Toorn A, and Nicolay K: MRI of hip prostheses using single-point methods: in vitro studies towards the artifact-free imaging of individuals with metal implants. Magn Reson Imaging 2004; 22(8): p. 1097-103. PMID: 15527996.

Rudisch A, Kremser C, Peer S, Kathrein A, Judmaier W, and Daniaux H: Metallic artifacts in magnetic resonance imaging of patients with spinal fusion. A comparison of implant materials and imaging sequences. Spine (Phila Pa 1976) 1998; 23(6): p. 692-9. PMID: 9549791.

Saito M, Ono S, Kayanuma H, Honnami M, Muto M, and Une Y: Evaluation of the susceptibility artifacts and tissue injury caused by implanted microchips in dogs on 1.5 T magnetic resonance imaging. J Vet Med Sci 2010; 72(5): p. 575-81. PMID: 20086326.

Shellock FG: Metallic neurosurgical implants: evaluation of magnetic field interactions, heating, and artifacts at 1.5-Tesla. J Magn Reson Imaging 2001; 14(3): p. 295-9. PMID: 11536406.

Shellock FG: MR imaging of metallic implants and materials: a compilation of the literature. AJR Am J Roentgenol 1988; 151(4): p. 811-4. PMID: 3048071.

Shellock FG: Prosthetic heart valves and annuloplasty rings: assessment of magnetic field interactions, heating, and artifacts at 1.5 Tesla. J Cardiovasc Magn Reson 2001; 3(4): p. 317-24. PMID: 11777223.

Starcukova J, Starcuk Z, Jr., Hubalkova H, and Linetskiy I: Magnetic susceptibility and electrical conductivity of metallic dental materials and their impact on MR imaging artifacts. Dent Mater 2008; 24(6): p. 715-23. PMID: 17884157.

Sutter R, Ulbrich EJ, Jellus V, Nittka M, and Pfirrmann CW: Reduction of metal artifacts in patients with total hip arthroplasty with slice-encoding metal artifact correction and view-angle tilting MR imaging. Radiology 2012; 265(1): p. 204-14. PMID: 22923720.

TDK: Magnet Design Data. Available from: http://www.tdk.co.jp/magnet_e/e371.pdf, accessed Jan. 12, 2016.

Toms AP, Smith-Bateman C, Malcolm PN, Cahir J, and Graves M: Optimization of metal artefact reduction (MAR) sequences for MRI of total hip prostheses. Clin radiol 2010; 65(6): p. 447-52. PMID: 20451011.

Volz S, Hattingen E, Preibisch C, Gasser T, and Deichmann R: Reduction of susceptibility-induced signal losses in multi-gradient-echo images: application to improved visualization of the subthalamic nucleus. Neuroimage 2009; 45(4): p. 1135-43. PMID: 19349229.

Wen Z, Fahrig R, Williams ST, and Pelc NJ: Shimming with permanent magnets for the x-ray detector in a hybrid x-ray/ MR system. Med Phys 2008; 35(9): p. 3895-902. PMCID: PMC2673662.

Wichmann W, Von Ammon K, Fink U, Weik T, and Yasargil GM: Aneurysm clips made of titanium: magnetic characteristics and artifacts in MR. AJNR Am J Neuroradiol 1997; 18(5): p. 939-44. PMID: 9159374.

\* cited by examiner

APPARATUSES AND METHODS FOR CANCELLATION OF INHOMOGENOUS MAGNETIC FIELDS INDUCED BY NON-BIOLOGICAL MATERIALS WITHIN A PATIENT'S MOUTH DURING MAGNETIC RESONANCE IMAGING

CROSS-REFERENCE TO RELATED APPLICATIONS

The present application is a continuation-in-part of U.S. non-provisional patent application Ser. No. 14/153,516 entitled "Apparatuses and Methods for Cancellation of Inhomogeneous Magnetic Fields Induced By Non-Biological Materials Within A Patient's Mouth During Magnetic Resonance Imaging," filed on Jan. 13, 2014, which application is incorporated by reference in its entirety.

FIELD OF INVENTION

The present invention relates generally to magnetic field homogenization during magnetic resonance imaging (MRI), and more specifically, but not by way of limitation, to apparatuses and methods for restoring losses in magnetic field homogeneity caused by non-biological materials within a patient's mouth.

BACKGROUND

Examples of using supplementary magnetic fields to correct MRI magnetic field homogeneity are disclosed in U.S. Pat. No. 6,968,982, and Wen Z., et. al, Shimming with Permanent Magnets for the X-Ray Detector in a Hybrid X-Ray/MR System, 35(9) Med. Phys. 3895 (2008), available at http://www.ncbi.nlm.nih.gov/pmc/articles/PMC2673662/.

During magnetic resonance imaging (MRI), magnetic fields can be induced in non-biological materials within a patient such as medical implants or orthodontic appliances (dental braces). Non-biological materials can be magnetized by the strong magnetic field of an MRI scanner, and the induced magnetization in the non-biological materials can become the source of a non-uniform magnetic field. These induced magnetic fields can disrupt MRI magnetic field ($B_0$) homogeneity and cause image intensity losses in regions near the non-biological materials and geometric distortions across the image. For example, during an MRI of the brain, non-biological materials located within the mouth of a patient may cause image intensity loss in the oral cavity and geometric distortions over the whole brain, specifically the orbits, hypothalamus, Circle of Willis, frontal lobe, and temporal lobes. Image loss and/or distortion is most severe for diffusion-weighted images, gradient echo images, and magnetic resonance angiography, and there is a loss of spectral resolution in magnetic resonance spectroscopy, as these techniques require a high degree of $B_0$ homogeneity.

Approximately 40% of the general population wears orthodontic appliances at some point in their life, particularly during adolescence. Many, if not most, dental braces comprise a common non-biological material which may be found within a patient's mouth. More particularly, approximately 95% of dental braces include brackets that comprise ferromagnetic stainless steel, as stainless steel is low cost, high strength, and durable. While orthodontic appliances, as well as other surgical implants, may be made of other more MRI-friendly materials such as plastic or titanium, these materials tend to be either too weak or expensive [19-32, 43-44]. Dental braces are particularly common in children, causing concern for children's hospitals, since around 80% of MRIs performed in a children's hospital involve imaging of the brain. For patients with dental braces, diffusion-weighted images and magnetic resonance angiography images are generally incomprehensible and therefore not performed. Such imaging techniques are critical for diagnosing many serious brain conditions, such as stroke.

One method for remedying the effect of non-biological materials on MRI imaging is to remove the non-biological materials from the patient before performing an MRI. In the case of dental braces, this involves removing the patient's braces prior to performing the MRI. Often times, as is the case with dental braces, removal of the non-biological materials is time consuming, expensive, and may be unavailable in emergency or after-hours situations. Other times, the MRI scan is performed with the non-biological materials in place, resulting in suboptimal image quality. In tumor patients requiring frequent follow-up MRI scans, removal of braces may lead to premature termination of orthodontic treatment. Current MRI technology seeks to remedy $B_0$ inhomogeneity through a technique known as image shimming, and most if not all scanners (e.g., 1.5 T (1.5 tesla) scanners) are capable of shim (e.g., linear shim). However, shimming is unable to remove image artifacts caused by non-biological materials within a patient. Other approaches include software correction [33-35], pulse sequence design and optimization [36-42], image unwrapping techniques [50], and sequence segmentation [51], which may be helpful for certain types of scans. However, these techniques generally fail to directly address inhomogeneities caused by non-biological materials within a patient (e.g., on a hardware rather than software level). While $B_0$ shimming using permanent magnets has been demonstrated in a 0.5 T X-ray/MRI hybrid system [46], permanent magnets have not been used to correct susceptibility artifacts caused by non-biological materials within a patient.

SUMMARY

Embodiments of the present apparatuses and methods can be configured to reduce image losses and/or distortions in MRIs that would typically otherwise be caused by non-biological materials within a user's mouth to an acceptable level for proper diagnosis from the MRI images. Some embodiments of the present apparatuses and methods use or include a plurality of permanent magnets disposed on an apparatus configured to be placed within a user's mouth (e.g., resembling a mouth guard) or outside and adjacent to the a user's mouth (e.g., resembling a mouth mask), where the magnets are located near non-biological materials within the user's mouth in an orientation such that the magnetization of the magnets opposes the MRI $B_0$ field when the apparatus is worn by the user. Through use of the present apparatuses, the induced inhomogeneous magnetic field originating from the non-biological materials can be substantially negated, leading to an increase in $B_0$ homogeneity and overall improvement of MRI image quality.

Some embodiments of the present apparatuses comprise: an arch-shaped body configured to be worn inside of a user's mouth such that the arch-shaped body follows a contour of at least some of the user's teeth; where the arch-shaped body comprises one or more sidewalls and a biting member, the biting member configured to be disposed between the user's mandibular and maxillary teeth, the one or more sidewalls angularly disposed relative to the biting member and configured to be coupled to a plurality of members comprising magnetically permeable material. Some embodiments further comprise: a handle configured to protrude from the user's mouth.

Some embodiments of the present apparatuses comprise: an arch-shaped body configured to be worn outside of a user's mouth such that the arch-shaped body follows a contour of the user's face; where the arch-shaped body comprises one or more sidewalls configured to be coupled to a plurality of members comprising magnetically permeable material. The arch-shaped body may be disposed outside the user's face without obstructing the user's airway. For example, the arch-shaped body may be disposed above or below the user's mouth. In some embodiments, the plurality of members are disposed substantially adjacent to the maxilla and/or mandible of the user.

Some embodiments of the present apparatuses comprise: a hybrid intraoral-external field correction device comprising a first arch-shaped body configured to be worn inside a user's mouth such that the arch-shaped body follows a contour of at least some of the user's teeth; where the arch-shaped body comprises one or more sidewalls and a biting member, the biting member configured to be disposed between the user's mandibular and maxillary teeth, the one or more sidewalls angularly disposed relative to the biting member and configured to be coupled to a plurality of members comprising magnetically permeable material; and a second arch-shaped body configured to be worn outside a user's mouth such that the arch-shaped body follows a contour of the user's face; where the arch-shaped body comprises one or more sidewalls configured to be coupled to a plurality of members comprising magnetically permeable material. In some embodiments, at least some of the plurality of members further comprise ferromagnetic material, such as, for example, magnets. In some embodiments, at least some of the one or more sidewalls of either or both the first and second arch-shaped body generate different magnetic moments.

In some embodiments of the external device, the correction magnets are embedded inside plastic strips which in turn are mounted on the arch shaped body outside the mouth. In some embodiments, these strips are divided into 4 columns for left molars, left incisors, right incisors and right molars. Each strip can be mounted on the frame individually.

In some of the present hybrid embodiments including intraoral and external components (which may be referred to as intraoral-external hybrid devices or systems), the intraoral component can be configured to mainly correct the magnetic field induced in incisor brackets (e.g., by including only or primarily magnets corresponding to the incisors), while the external component can be configured corrects both incisor and molar brackets (e.g., by including magnets corresponding to both the incisors and the molars).

In some embodiments of the present apparatuses, at least one of the one or more sidewalls comprises a curved surface, and the apparatus is configured to be worn by a user such that normal vectors along the surface lie substantially in a plane perpendicular to a magnetic field of a magnetic resonance imaging scanner.

Some embodiments of the present apparatuses further comprise: a plurality of members coupled to at least one of the one or more sidewalls, the plurality of members comprising magnetically permeable material. In some embodiments, at least some of the plurality of members comprise ferromagnetic material. In some embodiments, at least some of the plurality of members comprise magnets. In some embodiments, the members comprising magnets are coupled at substantially equal intervals along a length of the at least one of the one or more sidewalls. In some embodiments, the members comprising magnets are coupled to the at least one of the one or more sidewalls in two rows. In some embodiments, between 20 and 28 of the plurality of members comprise magnets. In some embodiments, at least one of the members comprising magnets comprises a material with a high intrinsic coercivity. In some embodiments, at least one of the members comprising magnets comprises neodymium. In some embodiments, at least one of the members comprising magnets is coated with nickel or nickel alloy and/or coated with plastic (e.g., parylene plastic). In some embodiments, at least one of the members comprising magnets has a long axis and a magnetization along the long axis, and the magnetization is configured to align in a substantially opposite direction to a magnetic field of a magnetic resonance imaging scanner. In some embodiments, at least some of the members comprising magnets are coupled to at least one of the one or more sidewalls such that the members comprising magnets are in close proximity to brackets of the user's dental braces when the apparatus is worn by the user. In some embodiments, at least one of the members comprising magnets is configured to have a substantially equal but opposite magnetic moment to a bracket of the user's dental braces. Some embodiments further comprise a layer of material configured to be coupled to the at least one of the one or more sidewalls such that the layer of material overlies each of the plurality of members. In some embodiments, the plurality of members is configured to partially restore losses in magnetic field homogeneity caused by non-biological materials within the user's mouth during magnetic resonance imaging. In some embodiments, the plurality of members is configured to reduce artifacts in magnetic resonance imaging images caused by non-biological materials within the user's mouth during magnetic resonance imaging. In some embodiments, the plurality of members is configured to substantially cancel out magnetic fields induced by non-biological materials within the user's mouth during magnetic resonance imaging. In some embodiments, a total magnetic moment generated by the plurality of members is substantially equal but opposite to the magnetic moment induced by non-biological materials within the user's mouth during magnetic resonance imaging. In some embodiments, the non-biological materials within the user's mouth comprise dental braces.

Some embodiments of the present apparatuses further comprise: a second arch-shaped body configured to be worn inside of a user's mouth such that the second arch-shaped body follows a contour of at least some of the user's teeth; where the second arch-shaped body comprises one or more sidewalls and a biting member, the biting member configured to be disposed between the user's mandibular and maxillary teeth, the one or more sidewalls angularly disposed relative to the biting member and configured to be coupled to a plurality of members comprising magnetically permeable material; and where the second arch-shaped body differs relative to the first arch-shaped body in at least one of: size and the configuration in which the plurality of members can be coupled to the one or more sidewalls.

Some embodiments of the present methods comprise: performing magnetic resonance imaging on a user having one or more magnets coupled to an apparatus disposed in the user's mouth or outside and adjacent to the user's mouth, the magnets configured to reduce artifacts in magnetic resonance imaging images caused by non-biological materials within the user's mouth during magnetic resonance imaging.

Some embodiments further comprise: adjusting the orientation of the user's head by manipulating a handle coupled to the apparatus.

Some embodiments of the present methods comprise: coupling a plurality of magnets to an arch-shaped body, the arch-shaped body configured to be worn by a user and the magnets configured to reduce artifacts in magnetic resonance imaging images caused by non-biological materials within the user's mouth during magnetic resonance imaging.

Some embodiments of the present apparatuses comprise a forehead support configured to be worn such that the forehead support follows the contours of the user's forehead. In some embodiments, the forehead support includes one or more openings to facilitate attachment and/or adjustment of a frame. In some embodiments, the frame further attaches to an arch-shaped body configured to be worn on the outside of a user's face.

Some embodiments of the present inventions comprise one or more straps joined to a forehead support, frame, and/or arch-shaped body in order to secure a forehead support, frame, and/or arch-shaped body to the outside of a user's face and/or head. In some embodiments, any or a part of any of an arch-shaped body, forehead support, frame, or one or more straps may be made of non-ferrous material, such as plastic.

Typically the external device fit tightly on patients such that the orthodontic brackets on the maxillary arch may be pressed against the skin in front of them with significant force. A maxillary mouth guard may be used with the external device to protect the skin. In the hybrid device described above, the intraoral component serves this function.

The magnetic moments induced in orthodontic appliances are different for different vendors and models of orthodontic appliances. Molar brackets have a larger range of variability compared with incisor brackets. Embodiments of the present devices (and/or apparatuses and/or systems) can be included in or presented as a kit containing exchangeable components with different magnetic moments. In use for MRI examinations, an appropriate device and/or exchangeable components can be selected and assembled from such a kit based, for example, on a calibration $B_0$ scan and computer analysis of the scan to best match the braces that the patient is actually wearing. For example, embodiments of the present kits can include multiple maxillary and/or mandible pieces for an intraoral device, each of which pieces having different magnetic moments. Similarly, embodiments of the present kits can include multiple strips or members with embedded magnets of different magnetic moments for each mounting position on the frame. By using one particular maxillary piece and/or mandibular piece, a large range of possible total magnetic moments of braces can be matched.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, 10, and 20 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

DETAILED DESCRIPTION OF ILLUSTRATIVE EMBODIMENTS

Excessive $B_0$ inhomogeneity on a macroscopic scale induced by non-biological materials within a user (a patient undergoing MRI)'s mouth, for example, ferromagnetic dental implants and dental braces, results in MRI artifacts [1-7] that can compromise the diagnostic value of MRI scans [8-9]. This is a special case of the more commonly known problem of susceptibility artifacts from surgical implants [10-18]. The magnitude of resulting loss or distortion depends on the type of MRI technique [14]. For example, because echo planar imaging (EPI) readout is sensitive to magnetic susceptibility effects, diffusion tensor imaging and diffusion-weighted images may be most affected. EPI uses low bandwidth per pixel for readout in the phase encoding direction, and even small inhomogeneities in the $B_0$ field can cause noticeable distortions in MRI images. In gradient echo images, artifacts can be observed when T2* is decreased to near the echo time (TE), especially when using larger voxel sizes. Typically, the artifacts manifest themselves as a loss of signal near the non-biological materials (e.g., the mouth in a patient with dental braces) and displacement of anatomical structures near the induced signal void (e.g., the hypothalamus area). Further from the signal void, the image distortions may be subtle and typically result in poor shimming. In magnetic resonance angiography, a frequency selective pulse is used to excite proton spins in the image volume. The presence of $B_0$ inhomogeneities can cause the resonance frequency of the proton spins near the non-biological materials to be shifted outside of the bandwidth of the frequency selective pulse, causing signal loss.

Figure 1:
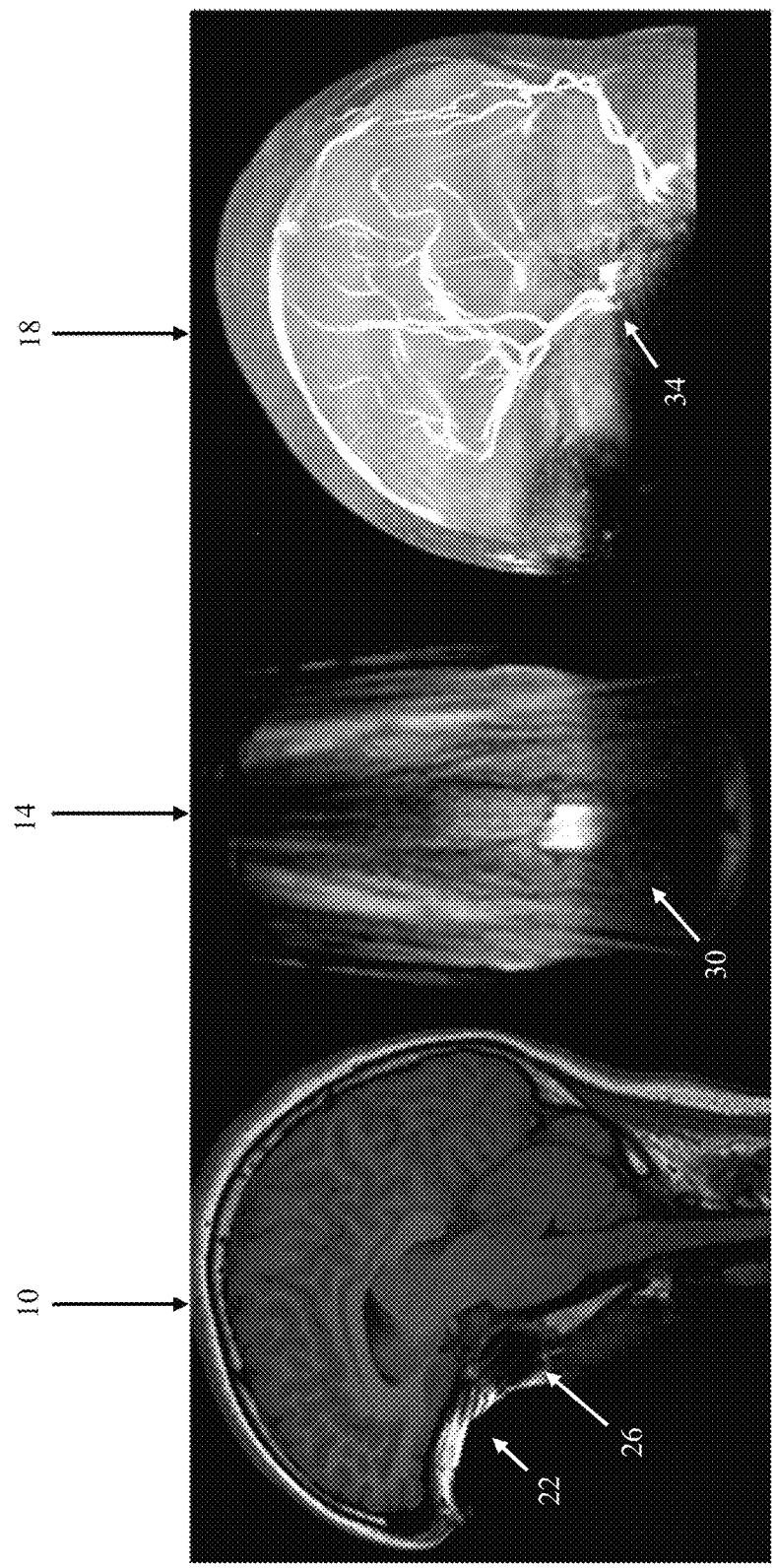
FIG. 1 depicts results from three different MRI techniques performed on a patient wearing dental braces.

FIG. 1 depicts image artifacts caused by non-biological materials within a patient's mouth in three different MRI scans: a sagittal T1 weighted image 10, an axial diffusion-weighted image of the area near the skull base 14, and a magnetic resonance angiography image 18. The patient undergoing the scans shown in FIG. 1 was wearing dental braces. In the sagittal T1 weighted image 10, the signal from the facial-orbital area 22 and the pituitary area 26 is severely distorted and/or missing. In the axial diffusion-weighted image 14, significant distortion can be seen near the base 30 of the skull. In the magnetic resonance angiography image 18, the signal is lost in the area 34 of the intracranial internal carotid arteries.

Figure 2A:
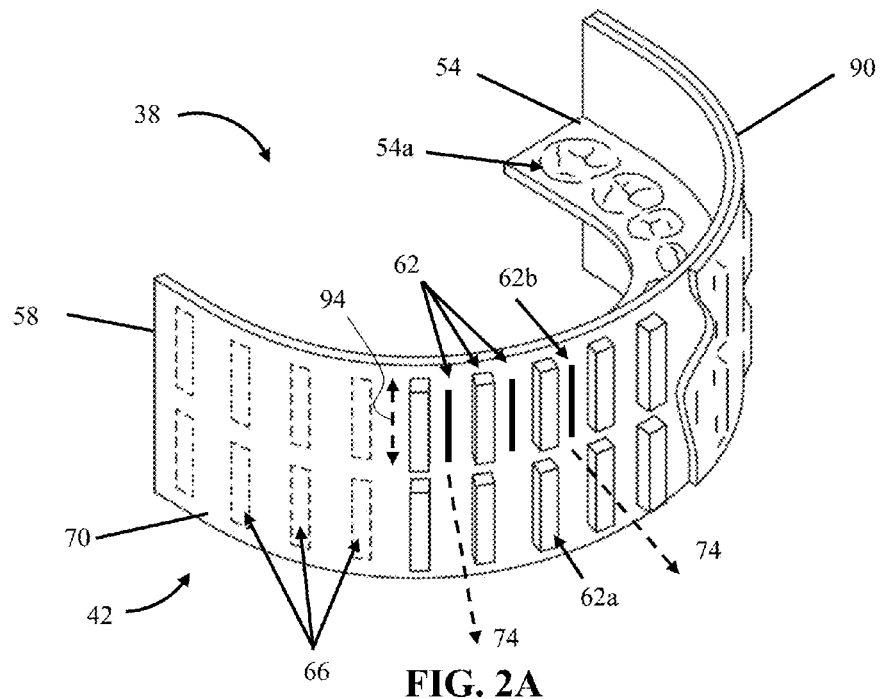
FIG. 2A is a cutaway perspective view of one embodiment of the present magnetic field correction devices.
Figure 2B:
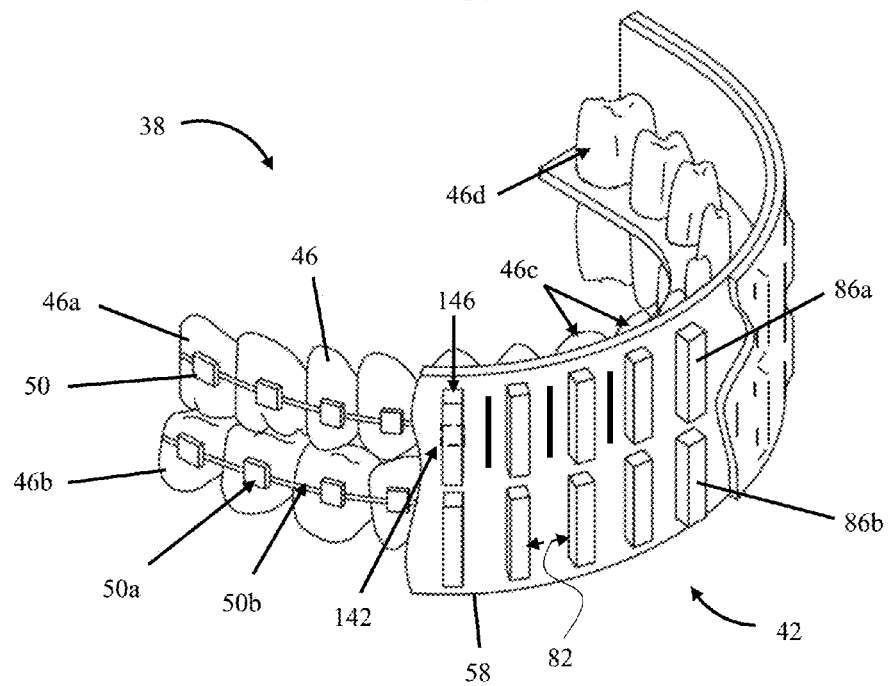
FIG. 2B is a second cutaway perspective view of the embodiment of FIG. 2A shown relative to a patient's teeth with dental braces as worn in a patient's mouth.

To correct images losses and distortions (e.g., as shown in FIG. 1), small permanent magnets may be placed near non-biological materials in a user's mouth to cancel out the magnetic fields induced by the non-biological materials. Factors such as the number of magnets, magnet size, magnet shape, magnet strength, and/or magnet position (e.g., orientation) may be selected to significantly reduce and/or eliminate susceptibility artifacts caused by orthodontic appliances or surgical implants in a user's mouth. Small pieces of ferromagnetic materials may be used in conjunction with the magnets to provide for fine adjustments to the magnetic field of the magnetic field devices. For example, FIG. 2A depicts a perspective view of one embodiment 38 of the present magnetic field correction devices or apparatuses. In the embodiment shown, device 38 comprises an arch-shaped body 42 configured to be worn inside of a user's mouth such that the arch-shaped body follows a contour of at least some of the user's teeth 46 (e.g., as shown in FIG. 2B). For example, arch-shaped body 42 can resemble a mouth guard which can be worn with dental braces 50 in place on the user's teeth. Through at least the selection of the arch-shaped body 42 size, embodiments of the present magnetic field correction devices can be configured to fit human mouths of various shapes and sizes. For example, older children generally have larger jaw sizes than younger children, and African Americans tend to have larger jaw sizes than Caucasians and Asians of similar sex and age (who tend to have smaller jaw sizes).

In the embodiment shown, arch-shaped body 42 defines a biting member 54 configured to be placed between the user's mandibular and maxillary teeth (e.g., maxillary teeth 46a and mandibular teeth 46b). Biting member 54 can be clamped by and between the user's mandibular and maxillary teeth during use such that arch-shaped 42 body remains substantially fixed relative to the user's teeth during an MRI procedure (e.g., clamped between a user's maxillary teeth 46a and mandibular teeth 46b as shown in FIG. 2B).

Figure 3:
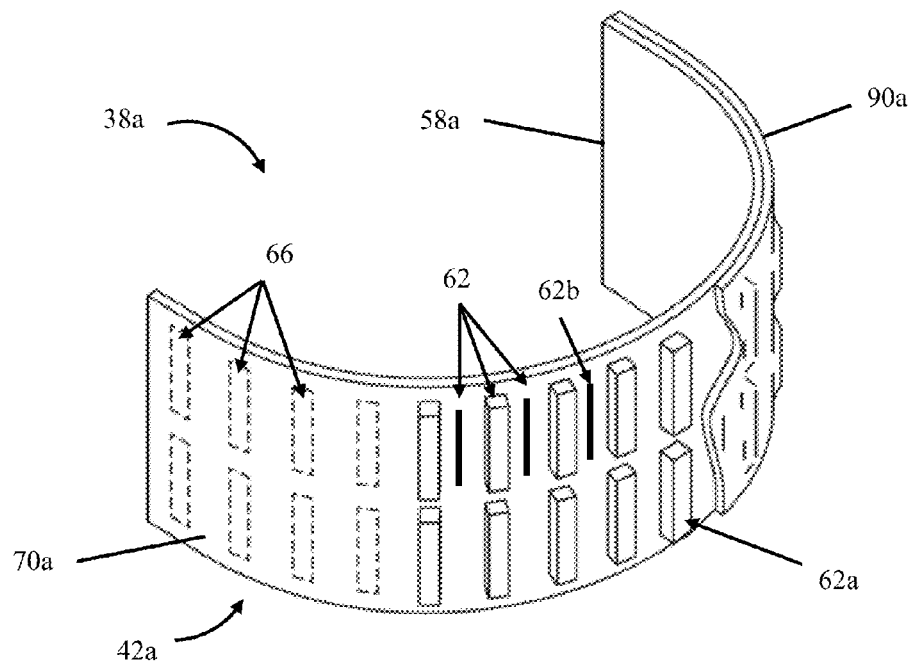
FIG. 3 is a cutaway perspective view of a second embodiment of the present magnetic field correction devices configured to be worn outside of and adjacent to a patient's mouth.

Referring now to FIG. 3, device 38a is substantially similar to device 38, with the primary exception that device 38a is configured to be worn outside of a user's mouth such that the arch-shaped body follows a contour of the user's face (e.g., arch-shaped body 42a is larger than arch-shaped body 42 to accommodate the lips of a user's mouth, and the back of sidewall 58a is configured to rest against a user's face near the user's mouth). Arch-shaped body 42a can be fixed to the user's face by any means which permit the functionality described in this disclosure, including, but not limited to, gluing, strapping, and/or through the user clamping a biting member similar to biting member 54 in device 38 (not shown in FIG. 3).

Figure 4:
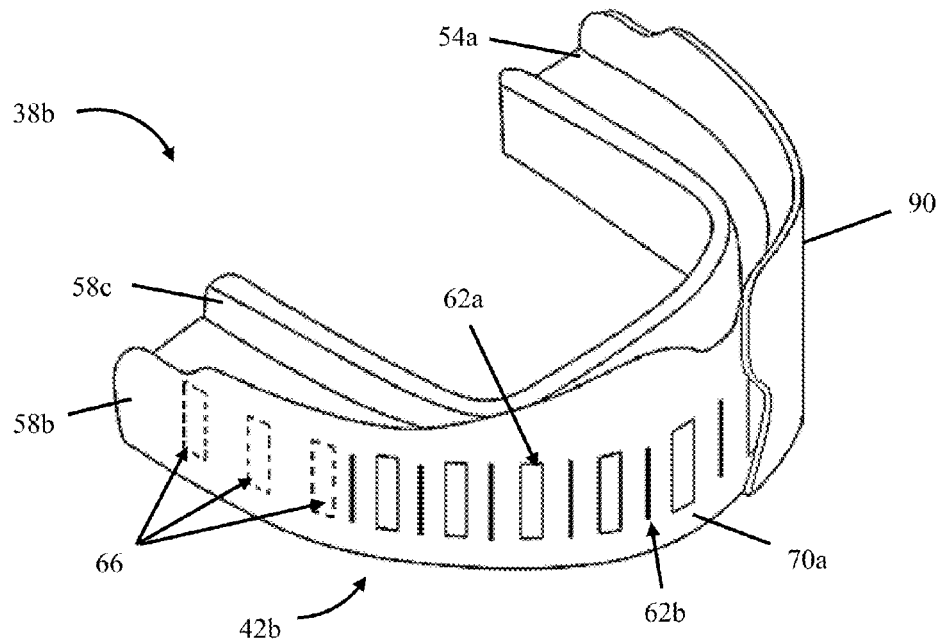
FIG. 4 is a cutaway perspective view of a third embodiment of the present magnetic field correction devices comprising two sidewalls.

Referring back to FIGS. 2A and 2B, in the embodiment shown, arch-shaped body 42 comprises one or more sidewalls 58 (e.g., one, as shown) that are angularly disposed relative to biting member 54 (e.g., as shown in FIG. 2A) and configured to be coupled to a plurality of members 62 (e.g., coupled at smooth locations 66, for example, with adhesive) comprising magnetically permeable material (e.g., magnets and/or ferromagnetic materials). Other embodiments can be configured to be coupled to a plurality of members 62 in any way which permits the functionality described in this disclosure, including, but not limited to, by pockets, recesses, slots, and/or the like disposed along surface 70 of sidewall(s) 58). In the embodiment shown, device 38 includes a single sidewall 58 that is substantially perpendicular to biting member 54. Other embodiments, such as device 38b shown in FIG. 4, can include two or more sidewalls 58 (e.g., front sidewall 58b and rear sidewall 58c). Other embodiments can have any number of sidewalls which permits the functionality described in this disclosure (e.g., upper and lower sidewalls, front and rear sidewalls, and/or the like). Referring back to FIGS. 2A and 2B, in the embodiment shown, sidewall 58 has a thickness of 2 millimeters (mm); however, in other embodiments, sidewall(s) 58 can have any thickness that permits the functionality described in this disclosure. In the embodiment shown, the shape of sidewall 58 is configured to substantially overlie at least some of maxillary teeth 46a and mandibular teeth 46b of a user (e.g., covering all of the mandibular and maxillary teeth of a user from central incisors 46c to second molars 46d, as shown in FIG. 2B). In other embodiments, by varying the height or location of sidewall(s) 58 relative to biting member 54, the sidewall(s) can be configured to substantially overlie only some of maxillary teeth 46a (e.g., device 38b) and/or only some of mandibular teeth 46b of the user. In the embodiment shown, at least one of sidewall(s) 58 comprises a curved planar surface 70. In this embodiment, curved planar surface 70 is configured such that normal vectors (e.g., 74) along the surface lie in a plane that is substantially perpendicular to a magnetic field of a magnetic resonance imaging scanner when device 38 is worn by a user.

In the embodiment shown, arch-shaped body 42 is molded to fit a representative user's mouth (e.g., through molded indentations 54a in biting member 54 that correspond to a representative user's teeth 46). For example, arch-shaped 42 body may be molded or otherwise formed from a dental impression (e.g., obtained from a dental model or a patient), which may be representative of the dental structure of a cross-section of (e.g., multiple) expected MRI patients. Suitable impression trays can be obtained from Ortho Technology. After the impression tray has been molded from a representative user's teeth, the front surface of the impression tray can be heated and bent outward to form a sidewall (e.g., 58) with a front surface (e.g., 70) having normal vectors (e.g., 74) that are substantially perpendicular to a magnetic field generated during magnetic resonance imaging. In other embodiments, the arch-shaped body may be formed from a thin sheet of plastic that is vacuum molded to fit a representative user's mandibular teeth 46b or maxillary teeth 46a (e.g., vacuum molded with a Biostar Vacuum former, available from Great Lakes Orthodontics). In these embodiments, the molding process can be performed twice such that the magnetic field correction devices comprise two arch-shaped bodies, one for the mandibular teeth of a representative user, and one of the maxillary teeth of a representative user (e.g., device 38b, which is molded to fit a representative user's maxillary teeth). In some embodiments, the present devices can comprise multiple arch-shaped bodies, sets of arch-shaped bodies (e.g., for two-piece devices), and/or devices. In such embodiments, the present apparatuses can comprise, for example, a larger device or arch-shaped body corresponding to a representative adult patient and a smaller device or arch-shaped body corresponding to a representative child patient (e.g., each device or arch-shaped body configured to be worn by a different expected user). Multiple devices and/or arch-shaped bodies can be disposed in a kit, and a physician can select the most appropriately-sized device for a given patient at the time of use (e.g., by selecting the device with the arch-shaped body that most closely corresponds to the given patient's dental structure). In other embodiments, the arch-shaped body is configured to be molded to fit a particular user's mouth at the time of use. For example, some embodiments of the present magnetic field correction devices (e.g., 38b) can comprise a thermoplastic material such that the arch-shaped body (e.g., 42b) can be heated to a deformable plastic state and placed within a user's mouth to contour to the user's teeth such that the arch-shaped body is contoured to the user's teeth and returns to a substantially rigid or inelastic state as it cools (e.g., such that the magnetic field correction device can be worn by a user similarly to as shown in FIG. 2B).

Figure 5:
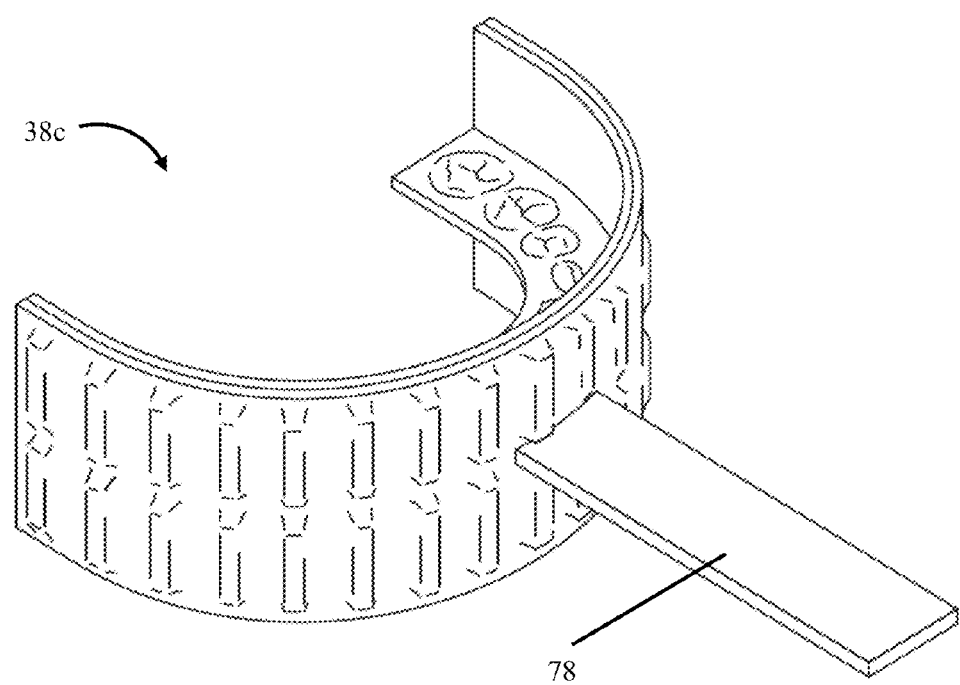
FIG. 5 is a perspective view of a fourth embodiment of the present magnetic field correction devices comprising a handle.

FIG. 5 depicts another embodiment 38c of the present magnetic field correction devices. Field correction device 38c is substantially similar to device 38, with the primary exception that device 38c comprises a handle 78 configured to protrude from a user's mouth (e.g., when the mouth guard is worn by a user as shown in FIG. 2B). Handle 78 can be used as a marker for optimally positioning the patient's head during an MRI which can be desirable for maximizing the effectiveness of magnetic field correction as discussed below.

Referring back to FIGS. 2A and 2B, in the embodiment shown, device 38 comprises a plurality of members 62 coupled to sidewall 58 where the members 62 comprise magnetically permeable material. In this embodiment, members 62 are coupled to sidewall 58 with adhesive. One example of a suitable adhesive is Triad Gel, manufactured by Dentsply GAC. In other embodiments, the members can be coupled to the sidewall(s) by any structure and/or method that permits the functionality described in this disclosure (e.g., through placement of members in receptacles disposed along surface 70 of the sidewall(s)). In the embodiment shown, at least some of the plurality of members comprise ferromagnetic material 62b (e.g., segments of stainless steel braces arch-wire). Ferromagnetic materials 62b may be placed, removed, and/or adjusted to provide fine adjustment of the magnetic field generated by magnetic field correction device 38. For example, magnets 62a may only be available in a fixed size and, in some instances, can cause overcorrection of MRI artifacts (e.g., by possessing a fixed size and/or magnetic moment that generates too strong of a corrective magnetic field). Thus, ferromagnetic materials (e.g., 62b) can enhance the induced magnetic field from non-biological materials within the user's mouth to correct any overcorrections caused by magnets 62a (e.g., by cancelling any excess magnetic field generated by magnets 62a). Additionally, the characteristics (e.g., size, shape, mass, material, and/or the like) of ferromagnetic materials 62b can be easily controlled (e.g., by selection, cutting, shaping, and/or the like) to provide fine adjustment of the magnetic field of the present devices (e.g., by changing the magnetic field induced in the ferromagnetic materials and thus device 38). In the embodiment shown, at least some of the plurality of members comprise magnets 62a (e.g., between 20 and 28 members comprise magnets). In some embodiments, twenty-eight (28) of members 62 comprise magnets (e.g., one magnet corresponding to each dental bracket in a typical orthodontic treatment consisting of 28 dental brackets). In other embodiments the present field correction devices may comprise any number of members, and any number of the members may comprise ferromagnetic materials and/or magnets (e.g., from four (4) to one hundred and twelve (112) members, of which from two (2) to fifty-six (56) comprise magnets). In the embodiment shown, members 62 comprising magnets 62a are coupled at substantially equal intervals 82 along a length (e.g., from left to right along an outer surface) of sidewall(s) 58 (e.g., each magnet is spaced a substantially equal distance 82 from each adjacent magnet). In the embodiment shown, magnets 62a are coupled to sidewall 58 such that the magnets form two rows 86a and 86b along sidewall 58. In this embodiment, device 38 also comprises a layer of material 90 coupled to sidewall 58 (e.g., coupled, as shown, with adhesive), where the layer of material 90 is configured to overlie each of plurality of members 62. Layer 90 can comprise a plastic sheet (e.g., a suitable plastic sheet can be obtained from Great Lakes orthodontics). Layer 90 can help ensure that members 62 do not directly contact tissue or saliva, and that members 62 are not swallowed if they come loose from sidewall 58.

In some of the present embodiments, at least one of the members 62 comprising magnets 62a comprises a material with a high intrinsic coercivity such that the at least one member can resist demagnetization in at least a 1.5 T MRI scanner (e.g., a minimum intrinsic coercivity of 20 kiloOersted (kOe)). For example, in the embodiment shown, all of members 62 that comprise magnets 62a comprise a magnetic material with an intrinsic coercivity of at least 20 kOe. In the embodiment shown, magnets 62a are configured such that the magnetization of each magnet is aligned in a direction that is substantially opposite to the expected direction of a $B_0$ field during an MRI of a patient wearing device 38. Therefore, in this embodiment, device 38 (via magnets 62a) is configured such that magnets 62a can experience a demagnetizing field when placed within an MRI scanner, resulting from both an internal demagnetization field (within magnets 62a) and an external ($B_0$) demagnetization field. In some embodiments, such as the one shown, at least one of members 62 comprising magnets 62a comprises a NdFeB (neodymium) magnet (e.g., a grade N38EH NdFeB neodymium magnet, available from Dexter Magnetic Technologies). In other embodiments, magnets 62a can comprise any material which permits the functionality described in this disclosure. When magnetized, neodymium magnets typically have a magnetization (magnetic moment per unit volume) comparable to that induced by non-biological materials (e.g., stainless steel dental braces brackets) inside an MRI scanner. Additionally, neodymium magnets possess a strong intrinsic coercivity and thus resist irreversible demagnetization in most MRI scanners (e.g., 1.5 T MRI scanners). An irreversibly demagnetized magnet will not return to its original magnetization when the external demagnetizing magnetic field (e.g., the MRI magnetic field) is removed; however, irreversibly demagnetized magnets can have their magnetization restored through application of external magnetizing fields.

Figure 6:
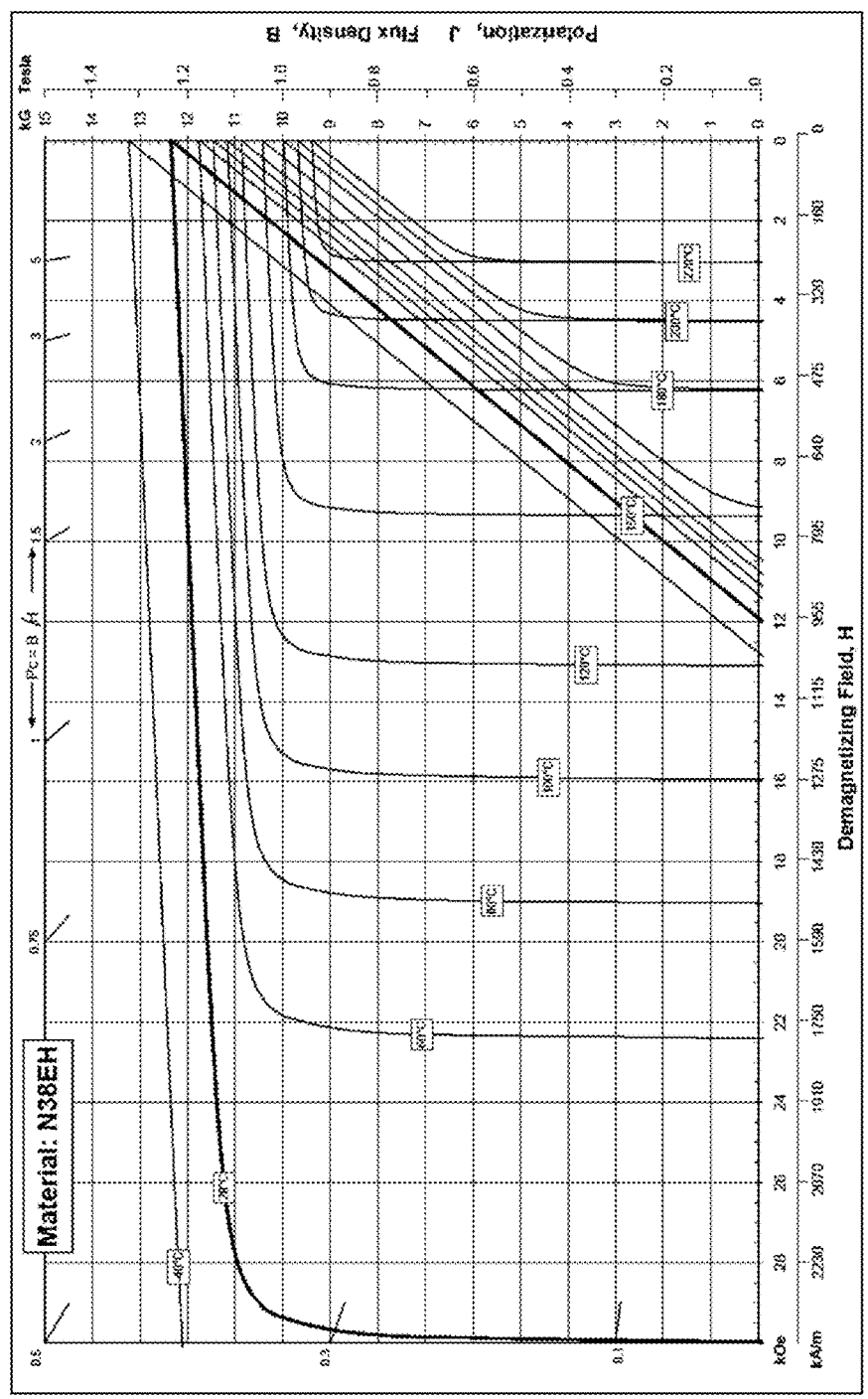
FIG. 6 is a graph of the demagnetization curve for a NdFeB (neodymium) magnet.

FIG. 6 is a graph of the demagnetization curve for an N38EH neodymium magnet [45]. As shown, demagnetization is temperature dependent, and at 20° Celsius (° C.) (indicated by the darkened line) the intrinsic coercivity of an N38EH magnet is 30 kOe, which represents the demagnetizing field strength at which the magnetization of the N38EH magnet becomes zero. The "knee point" for a magnet is the demagnetizing field strength at which the magnet will begin to irreversibly lose magnetization. Below the knee point, the magnet operates in the linear demagnetization regime, and magnetization can be restored when the demagnetizing field strength is reduced to zero (e.g., after an MRI scan is complete and the patient is removed from the scanner). The knee point is not sharply defined, and generally is located in a range from half of the intrinsic coercivity to just below the intrinsic coercivity of a material. For example, for an N38EH magnet at 20° C., below 26 kOe, the flux density (B) vs. demagnetizing field (H) curve is nearly linear, and the polarization (J) remains nearly constant. Therefore, 26 kOe approximates the knee-point for an N38EH magnet at 20° C. At body temperature (approximately 37° C.), the intrinsic coercivity of an N38EH magnet is approximately 27 kOe and the knee point is above 20 kOe, therefore N38EH magnets (e.g., 62a) will not irreversibly lose magnetization in a 1.5 T MRI scanner (the most common MRI field strength) for a permeance coefficient ($p_c$) greater than 2 (e.g., at these values, the magnet is operating in the linear regime of the demagnetization curve) [45, 49]. However, an N38EH magnet can irreversibly lose magnetization at 37° C. (body temperature) in more powerful MRI scanners (e.g., 3 T or 7 T MRI scanners). In such powerful MRI scanners, demagnetization of the magnets will occur within seconds; however, the magnets can regain magnetization through placement in an external magnetizing magnetic field. Embodiments of the present magnetic field correction devices that have been demagnetized by large demagnetizing fields (e.g., 3 T or 7 T MRI scanners) may be re-magnetized and can be used again in 1.5 T (or lower $B_0$) MRI scanners. Magnets with yet higher intrinsic coercivities may be available in the future, and may be used with the present field correction devices to restore $B_0$ homogeneity in 3 T, 7 T, and/or more powerful MRI scanners.

Referring back to FIGS. 2A and 2B, in the embodiment shown, members 62 comprising magnets 62a are coated with nickel or nickel alloy to prolong the shelf-life of the magnets and to reduce the potential toxicity of NdFeB magnets [56-57]. For example, such nickel or nickel alloy coated magnets have safely been used in dental devices [48, 58-59]. In this embodiment, the nickel or nickel alloy coating is approximately 0.015 mm thick. In the embodiment shown, at least one of the plurality of members 62 comprising magnets 62a has a long axis 94 and a magnetization along the long axis. In the embodiment shown, long axis 94, and thus the direction of magnetization, of each magnet 62a is configured to align in a substantially opposite direction to the direction of a magnetic field ($B_0$) of a magnetic resonance imaging scanner when device 38 is worn by a user. Long and thin magnets (e.g., 62a) generate a relatively smaller internal demagnetization field (within magnets 62a) than magnets comprising other shapes. In other embodiments, the magnets 62a can comprise any shape that permits the functionality described in this disclosure. In some embodiments, magnets 62a can be obtained before they are magnetized, and can thereafter be magnetized (e.g., by placing the magnets in a 7 T human or 9.4 T animal MRI scanner) before using device 38. Such embodiments can provide convenience by preventing the magnets from attracting one another while handling the magnets and/or assembling the device.

Permanent magnets (e.g., 62a) experience a torque and a force when inside an MRI scanner, due to the $B_0$ field, and the magnitudes of these phenomena should be limited to ensure patient comfort and safety. The torque felt by a patient from a magnetic field correction device is given by the following cross-product:

$$T = m \times B_0 \quad (1)$$

where m is a vector representing the total magnetic moment of the magnetic field correction device, $B_0$ is a vector representing the MRI magnetic field, and T is a vector representing the total torque felt by a patient from a magnetic field correction device. Based on Table 1 (discussed in more detail below), the total magnetic moment of a magnetic field correction device that corresponds to a dental model with 28 Maestro braces brackets is approximately 0.143 Ampere-square meters (A·m$^2$). For example, such a magnetic field correction device may comprise 28 N38EH NdFeB magnets (e.g., a magnet corresponding to each bracket).

In a 1.5 T MRI machine, it can be shown that:

$$T = 0.2 * \sin(\Theta) \quad (2)$$

where T is torque in Newton-meters (Nm), and $\Theta$ is the angle between the $B_0$ field ($B_0$) and the magnetic moment (m). As can be seen from Eq. 2, when the magnets (e.g., 62a) are positioned such that the resulting magnetic moment from the magnets is oriented 180° from the $B_0$ field, the torque experienced by the patient is zero. Human neck muscles use approximately 5-6 Nm of torque to counter gravitational forces acting on the head [52]. Additionally, the human biting force, even at 7-12 years of age, is at least 350 Newtons (N) [53]. Assuming a leverage distance of 7 centimeters (cm) (e.g., the approximate width of some embodiments of the present magnetic field correction devices from one side of the distal portion of the arch-shaped body 42 to the other), the human jaw can resist a torque of approximately 25 Nm. Therefore, the maximum torque experienced by a patient wearing an embodiment of the present magnetic field correction devices (e.g., 38) can be easily overcome by the neck and jaw muscles.

The force experienced by a permanent magnet (e.g., 62a) within an MRI machine is directly proportional to the gradient of the $B_0$ field. Therefore, the largest force occurs while the patient is moving in and out of the scanner. For a large 3 T MRI magnet, the maximum $B_0$ gradient is 5.2 teslas per meter (T/m) [55]. In a 1.5 T scanner, the maximum $B_0$ gradient is roughly half of that for a 3 T MRI, or approximately 2.6 T/m. Multiplying this value by the total magnetic moment of magnetic field correction device that corresponds to a dental model with 28 Maestro braces brackets (e.g., which may comprise 28 NdFeB magnets, as described above) (provided above) results in an approximated maximum force experienced by a patient wearing such an embodiment of the present magnetic field correction devices of only 0.37 N.

Figure 7:
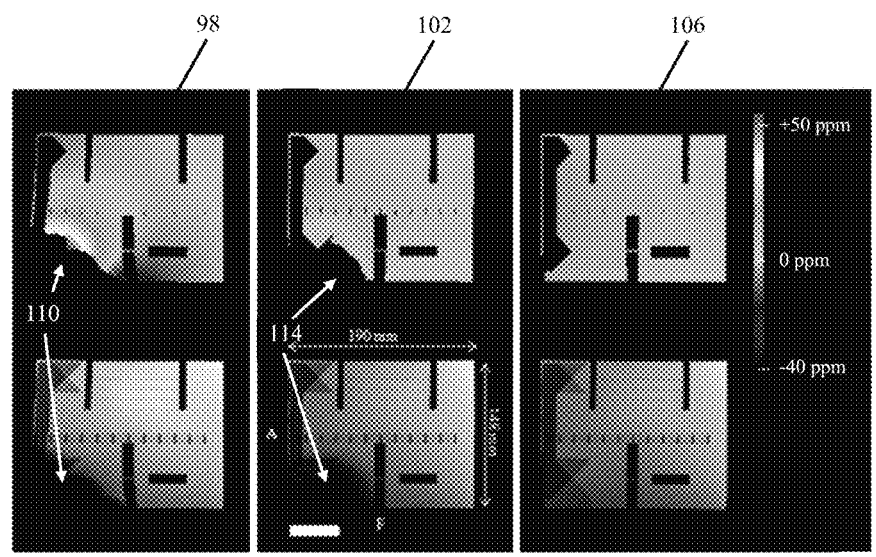
FIG. 7 depicts sagittal $\Delta B_0$ maps for a simulated patient with dental braces and without a magnetic field correction device, with dental braces and with a magnetic field correction device, and without dental braces and without a magnetic field correction device.
Figure 8:
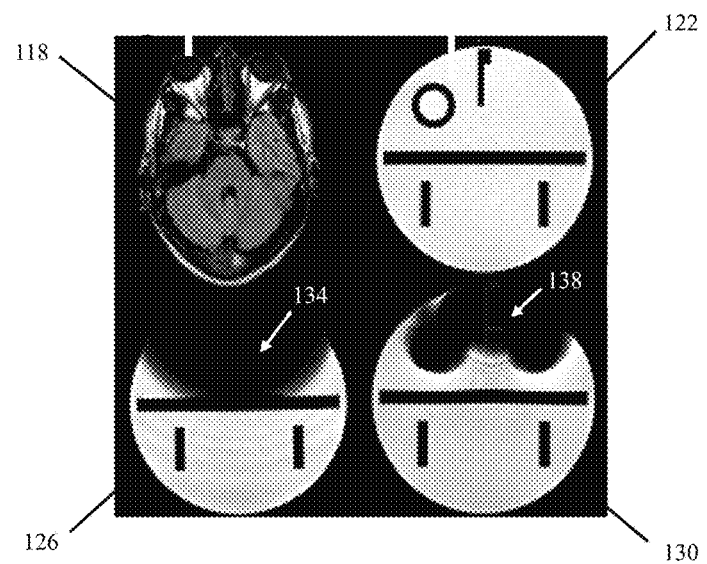
FIG. 8 depicts a magnetic resonance angiography brain slice for a patient, along with a corresponding image for a simulated patient without dental braces and without a magnetic field correction device, with dental braces and without a magnetic field correction device, and with dental braces and with a magnetic field correction device.
Figure 10:
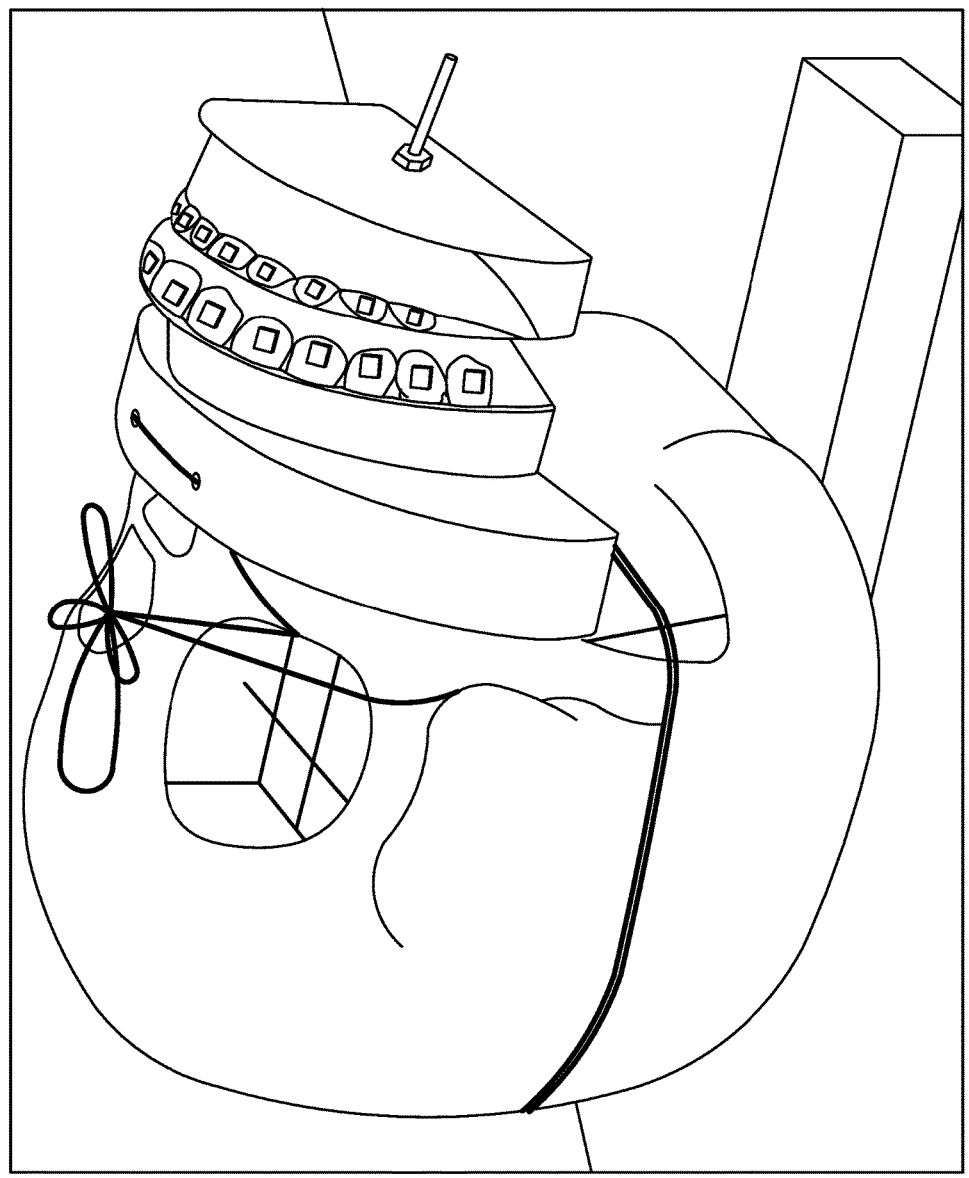
FIG. 10 is a perspective view of a head phantom with dental braces and the intraoral device.

Referring back to FIGS. 2A and 2B, in the embodiment shown, the plurality of members 62 is configured to partially restore losses in magnetic field homogeneity caused by non-biological materials within the user's mouth (e.g., dental braces 50) during magnetic resonance imaging. FIG. 7 depicts sagittal $\Delta B_0$ maps, which indicate magnetic field ($B_0$) homogeneity, including a map 98 for a simulated patient with dental braces and without a magnetic field correction device, a map 102 for a simulated patient with dental braces and with a magnetic field correction device, and a map 106 for a simulated patient without dental braces and without a magnetic field correction device. To simulate a patient with dental braces, a realistic dental brace model from Damon System can be used, which has twenty-eight (28) stainless steel dental braces brackets mounted on twenty-eight (28) model teeth. The head phantom (used by the American College of Radiology for accreditation [47], an example of which is shown in FIGS. 7 and 8) can be positioned in an eight channel SENSE head coil, and the dental model can be positioned next to the phantom to simulate a patient in a supine position. More recent work used a 3D printed head phantom (FIG. 10). The $\Delta B_0$ sagittal maps can be measured from the phase difference of two images with different echo times (e.g., 4.6 milliseconds (ms) and 5.0 ms) acquired with a fast field echo (FFE) sequence, and low signal areas in the amplitude images can be excluded. The sagittal map 98 for the simulated patient with dental braces shows large regions 110 of image loss, as well as image distortion across the map (e.g., compare map 98 with map 106). For map 98, the peak-to-peak $\Delta B_0$ is 81.0 parts-per-million (ppm), and the standard deviation is 9.1 ppm. The relatively large peak-to-peak $\Delta B_0$ value is indicative of a loss of homogeneity in the MRI magnetic field due to the magnetic fields induced by the dental braces. Sagittal $\Delta B_0$ map 102 is of a simulated patient with dental braces and with one of the present magnetic field correction devices (e.g., 38) disposed within the simulated patient's mouth. Map 102 shows a reduced region 114 of image loss, as well as significantly reduced distortion throughout the image (e.g., compare map 102 with map 98). For map 102, the peak-to-peak $\Delta B_0$ value is 20.3 ppm, and the standard deviation is 1.4 ppm. The significant reduction in peak-to-peak $\Delta B_0$ from map 98 to map 102 is indicative of the magnetic field correction device partially restoring homogeneity to the MRI magnetic field. Sagittal map 106 for the simulated patient without braces and without a magnetic field correction device has a peak-to-peak $\Delta B_0$ value of 6.6 ppm and a standard deviation of 1.2 ppm. As shown in FIG. 7, the magnetic field correction devices can be configured to significantly improve $B_0$ homogeneity (e.g., by varying at least the number, size, shape, strength, and/or positioning (e.g., orientation) of magnets 62a and/or ferromagnetic materials 62b).

Referring back to FIGS. 2A and 2B, the plurality of members 62 is further configured to reduce artifacts in magnetic resonance imaging caused by non-biological materials within the user's mouth (e.g., dental braces 50) during magnetic resonance imaging. FIG. 8 depicts a magnetic resonance angiography brain slice 118 for a patient, along with a corresponding image 122 for a simulated patient without dental braces and without a magnetic field correction device, image 126 for a simulated patient with dental braces and without a magnetic field correction device, and image 130 for a simulated patient with dental braces and with a magnetic field correction device. Axial brain slice 118 is through the middle of the pons, where magnetic resonance angiography is particularly important from a clinical perspective. As shown image 122 for a simulated patient without braces and without a magnetic field correction device is clear, and there is no significant image loss or distortion. In image 126 for a simulated patient with dental braces and without a magnetic field correction device, there is a large region 134 of image loss, as well as distortions throughout the image. In magnetic resonance angiography (as used in FIG. 8), a frequency selective radio frequency (RF) pulse is used for signal excitation or suppression. During these imaging techniques, non-biological materials (such as dental braces) can result in artifacts (e.g., region 134) by shifting the water resonance position to outside of the excitation bandwidth. With an embodiment of the present magnetic field correction devices (e.g., 38) disposed in the simulated patient's mouth along with dental braces, image 130 shows a large reduction in both image loss in the vicinity of the dental braces 138, as well as a reduction in image distortion throughout the image (e.g., compare image 130 with image 126). As shown, the present magnetic field correction devices can be configured to reduce artifacts (e.g., region 134) in magnetic resonance imaging caused by non-biological materials within the user's mouth (e.g., dental braces 50) during magnetic resonance imaging (e.g., by varying at least the number, size, shape, strength, and/or positioning (e.g., orientation) of magnets 62a and/or ferromagnetic materials 62b)

Referring back to FIGS. 2A and 2B, in the embodiment shown, the non-biological materials within the user's mouth comprise dental braces (e.g., dental braces 50). An example of such dental braces are manufactured by Ormco. In the embodiment shown, members 62 comprising magnets 62a are coupled to sidewall 58 such that, if device 38 is worn (e.g., as shown in FIG. 2B) in the mouth of a user with dental braces, each of magnets 62a is in close proximity to a different one of brackets 50a of the user's dental braces 50 (e.g., magnet 146 is in close proximity to bracket 142 in FIG. 2B). As used in this disclosure, "close proximity" means between 0 mm and 15 mm between the magnet and the bracket. Both guide-wire 50b and brackets 50a of dental braces 50 can contribute to an induced magnetic field generated during MRI, but the contributions from the guide-wire are generally small. Additionally, it is relatively easy to remove the guide-wire from the patient's braces before performing an MRI scan. Therefore, the induced magnetic field may be dominated by the contributions from the brackets. Thus, the total induced magnetic field by the dental braces can be approximated as the sum of the magnetic dipole field from each of brackets 50a. In an ideal case, a magnet would be positioned precisely in the same location as each dental bracket with an equal but opposing magnetic moment to the bracket to completely cancel out the magnetic moment induced by each individual bracket; in practice, however, this is difficult if not impossible. Therefore, placing the magnets as close as practicable to brackets can be desirable.

In the embodiment shown, each member 62 comprising a magnet 62a is configured to have a substantially equal but opposite magnetic moment to a bracket (e.g., 142) on the user's dental braces 50. Examples of commonly used brackets for dental braces are available from Dentsply GAC, 3M Unitek, and American Orthodontics. Each tooth in a patient's mouth has a unique anatomical shape, and therefore brackets in a set of dental braces can comprise different designs from one another (e.g., to provide optimal bonding to each individual tooth). Additionally, brackets made in different manufacturing batches may not be identical and can possess variations in shape, weight, and therefore induced magnetic moment within an MRI scanner. The magnetic properties of a dental braces bracket can also vary with bracket orientation. Since variability of dental braces bracket orientation may be inevitable, given neither a tooth, nor the dental braces bracket mounted on the tooth will be perfectly straight, it can be desirable to determine the induced field pattern for a given dental braces bracket in multiple orientations (not just one orientation that corresponds to straightly mounting the bracket on a straight tooth).

The magnetic properties of a given dental braces bracket including the effect of orientation and manufacturing-related variability on the induced magnetic dipole, as well as induced magnetic dipole amplitude can be determined. MRI machines are sensitive to the z-component of induced magnetic fields, and dental braces bracket magnetic susceptibility can be anisotropic: dental braces brackets can generate different non-zero magnetic moments in the x and y directions, and each can generate a magnetic field with a z-component. To measure the magnetic properties of a dental braces bracket, a 2 liter (l) spherical glass flask containing a water solution of NaCl doped with ProHance can be used. A dental bracket can be mounted, in the desired orientation, on the tip of a plastic rod, which can be inserted into the center of the flask through a thin nuclear magnetic resonance (NMR) spectroscopy tube. The $B_0$ field can then be mapped using a three-dimensional (3D) gradient echo sequence at two echo times of 3.5 ms and 3.8 ms respectively, utilizing the following parameters: 3D coronal FFE, cubic voxel size of 8 mm$^2$, field of view of 224 pixels by 224 pixels, 75 slices, water-fat shift of 0.26 pixels, repetition time (TR) of 10 ms, flip angle of 10°, readout along the right-to-left (RL) direction, number of signal averages (NSA) of 1, and an acquisition time of 2 minutes (min) and 50 seconds (s). The 3D field map can then be obtained from the difference of phase images and modeled as a magnetic dipole with the equation:

$$B_z = \frac{\mu_0}{4\pi} \frac{3n_z(n \cdot m) - m_z}{|x|^3} \tag{3}$$

where x is a displacement vector from the location of the dipole to a point in space where the field is measured, n is a unit vector along the direction of x, and m is a vector representing the induced magnetic moment to be determined (e.g., through a least squares fitting routine). Through this process, the magnetic properties of each dental braces bracket can be measured individually in multiple orientations. The above method can also be used to determine the magnetic properties of a magnet.

Table 1 provides the induced magnetic moment of a Maestro UL1 dental bracket for five orientations in a 1.5 T MRI scanner.

TABLE 1

| Orientation Dependence of the Magnetic Moment of a Maestro UL1 Dental Bracket in a 1.5T MRI Scanner | | | | | | | | | | | | | | |
|---|---|---|---|---|---|---|---|---|---|---|---|---|---|---|
| Straight | | | −30° Pitch Angle | | | 30° Pitch Angle | | | −30° Roll Angle | | | 30° Roll Angle | | |
| $m_x$ | $m_y$ | $m_z$ | $m_x$ | $m_y$ | $m_z$ | $m_x$ | $m_y$ | $m_z$ | $m_x$ | $m_y$ | $m_z$ | $m_x$ | $m_y$ | $m_z$ |
| −0.05 | −0.05 | 5.11 | −0.04 | −0.33 | 5.11 | −0.03 | 0.29 | 5.16 | −0.03 | −0.04 | 4.96 | −0.02 | −0.02 | 5.14 |

Units of magnetic moment are in $10^{-3}$ A·m$^2$, and the bracket orientation angles are defined from the patient's perspective and correspond to a patient lying supine and head first into the MRI magnet. The x-axis points to left, the y-axis is along the anterior direction, and the z-axis points to the patient's foot. Table 1 shows that $m_x$ and $m_y$ are much smaller than $m_z$, and $m_z$ is not sensitive to orientation, for example, the coefficient of variation of $m_z$ is about 1.5% for this Maestro UL1 dental bracket. Therefore, in embodiments in which at least one of the plurality of members 62 comprising a magnet 62a is configured to have a substantially equal but opposite magnetic moment to a bracket (e.g., a Maestro UL1 dental bracket, as described in Table 1, as bracket 142) on the user's dental braces 50 (e.g., magnetic field correction device 38), the at least one member is a magnet with a magnetic moment ($m_z$) of approximately −5.11 to −5.14 $10^{-3}$ A·m$^2$.

In the embodiment shown, members 62 are further configured to substantially cancel out magnetic fields induced by non-biological materials within the user's mouth during magnetic resonance imaging (e.g., by configuring members 62 comprising magnets 62a such that magnets 62a have a substantially equal, but opposite, magnetic moment to the magnetic moment induced by the respective dental braces brackets as described above).

In the embodiment shown, the total magnetic moment generated by members 62 is substantially equal but opposite to the magnetic moment induced by non-biological materials within the user's mouth during magnetic resonance imaging. For example, if the non-biological materials comprise dental braces (e.g., 50), it may not be practical to include a magnet for each corresponding bracket (e.g., 142) on the dental braces. Therefore, the total magnetic moment of the magnetic field correction device can be configured to match the magnetic moment induced by the non-biological materials (e.g., braces 50) within the user's mouth, regardless of the number of members 62 (e.g., by varying at least the number, size, shape, strength, and/or positioning (e.g., orientation) of magnets 62a and/or ferromagnetic materials 62b). For example, using the data from Table 1 and roughly approximating each bracket as a Maestro UL1 bracket, the total magnetic moment induced by 28 brackets is approximately 0.143 A·m$^2$. Therefore, in embodiments of the present magnetic field correction devices where the plurality of members 62 are configured to generate a substantially equal but opposite magnetic moment to that induced by non-biological materials within the user's mouth during an MRI (e.g., braces 50 consisting of Maestro UL1 brackets), the plurality of members can have a total magnetic moment of approximately −0.143 A·m$^2$.

From data depicted in Table 1, computer simulations can be performed to quantify $B_0$ inhomogeneity and the dependence of magnetic field correction effectiveness on head orientation, magnet strength, and/or magnet location. To perform a computer simulation, an existing 3D T1 weighted magnetic resonance image set of the brain can be chosen (e.g., of a typical 14 year old boy). Twenty-eight magnetic dipoles can be placed in the position of teeth on the MRI to represent the brackets on dental braces, and each dipole can be assumed to have the $m_z$ value from Table 1. The brain can then be segmented into compartments, and for each region the range, mean, and standard deviation of the induced magnetic field can be calculated.

The central brain in Table 2 consists of the corpus callosum, basal ganglia, and thalami. As shown in Table 2, even in less than ideal conditions (e.g., magnets 62a placed relatively far away from dental braces brackets 50a), $B_0$ inhomogeneity can be significantly decreased by the present magnetic field correction devices, and accurate head orientation and magnet (e.g., 62a) magnetization can be desirable to help achieve magnetic field correction effectiveness.

Some embodiments of the present methods comprise performing an MRI on a user (e.g., with an MRI scanner such as a 1.5 T Phillips Achieva) having one or more magnets (e.g., 62a) coupled to an apparatus (e.g., magnetic field correction device 38, 38a, 38b, or 38c) disposed in the user's mouth (e.g., as shown in FIG. 2B) or outside and adjacent to the user's mouth (e.g., device 38a, when worn by a user), where the magnets are configured to reduce artifacts in magnetic resonance imaging images caused by non-biological materials within the user's mouth during magnetic resonance imaging (e.g., in a similar fashion as described above). Further embodiments comprise adjusting the orientation of the user's head by manipulating a handle (e.g., 78) coupled to the apparatus (e.g., magnetic field correction device 38a) and configured to protrude from the user's mouth when the apparatus is worn by the user (e.g., worn, as shown, in FIG. 2B).

Other embodiments of the present methods comprise coupling a plurality of magnets (e.g., 62a) to an arch-shaped body (e.g., 42) configured to be worn by a user (e.g., worn, as shown, in FIG. 2B) and the magnets (e.g., 62a) configured to reduce artifacts in magnetic resonance imaging images caused by non-biological materials (e.g., dental braces 50) within the user's mouth during magnetic resonance imaging (e.g., in a similar fashion as described above). In further embodiments, the magnets are selected and placed on the arch-shaped body (e.g., 42) after determining the magnetic moment induced by non-biological materials within a user's mouth through use of an MRI measurement (as described above or through an iterative process in which an MRI is performed on the patient and magnet 62a number, size, shape, strength, and/or positioning (e.g., orientation) are adjusted until the MRI scans achieve a quality necessary for diagnostic value). In other embodiments, an apparatus comprising multiple arch-shaped bodies, sets of arch-shaped bodies, and/or devices can be provided. In such embodiments, the arch-shaped bodies and/or devices can have different magnetic characteristics (e.g., different magnetic

TABLE 2

Magnetic Field Inhomogeneity (ppm) due to Dental Braces and Magnetic Field Correction Effectiveness for Various Head and Magnet Locations, and Magnet Strengths

|  |  | Frontal Lobe | Temporal Lobe | Brainstem | Pituitary glands | Central Brain | Cerebellum |
|---|---|---|---|---|---|---|---|
| Braces without correction | $B_0$ range | 0.9, 44.1 | −3.8, 30.4 | −11.2, 5.4 | 7.9, 13.8 | 1.1, 17.5 | −9.9, 0.2 |
|  | mean ± sd | 8.9 ± 6.3 | 2.3 ± 4.5 | −1.4 ± 3.2 | 10.9 ± 1.5 | 5.3 ± 3.3 | −3.3 ± 1.5 |
| Shift magnets 5 mm outward | $B_0$ range | −1.3, 1.9 | −0.7, 4.1 | −0.3, 0.2 | −0.3, 0.0 | 0.0, 0.8 | −0.3, 0.0 |
|  | mean ± sd | 0.2 ± 0.3 | 0.3 ± 0.5 | −0.1 ± 0.1 | −0.1 ± 0.1 | 0.2 ± 0.1 | −0.1 ± 0.1 |
| Pitch head by 10° | $B_0$ range | −4.4, −0.3 | −7.7, −0.3 | −2.9, −0.4 | −4.3, −3.3 | −3.0, −0.6 | −2.2, −0.0 |
|  | mean ± sd | −1.0 ± 0.6 | −1.6 ± 1.2 | −1.7 ± 0.4 | −3.8 ± 0.2 | −1.4 ± 0.4 | −0.5 ± 0.3 |
| 10% weaker magnets | $B_0$ range | −2.2, 1.8 | −6.6, 0.6 | −3.5, −1.1 | −3.7, −2.7 | −2.0, −0.1 | −2.6, −0.4 |
|  | mean ± sd | −0.0 ± 0.5 | −1.3 ± 0.8 | −2.1 ± 0.4 | −3.1 ± 0.2 | −0.8 ± 0.3 | −1.1 ± 0.4 |
| 10% stronger magnets | $B_0$ range | −7.7, −0.5 | −9.0, −0.1 | −2.9, 0.4 | −5.4, −3.8 | −3.9, −0.5 | −2.1, 0.4 |
|  | mean ± sd | −1.6 ± 1.0 | −1.3 ± 1.1 | −1.4 ± 0.6 | −4.6 ± 0.3 | −1.6 ± 0.6 | 0.3 ± 0.3 | moments), different configurations (e.g., a different configuration in which magnetically permeable members 62 can be coupled to the arch-shaped bodies, such as, for example, differing smooth locations 66) and/or different physical characteristics (e.g., size, shape, contour, curvature, and/or the like). The magnetic moment induced by non-biological materials within a patient's mouth can be determined through use of an MRI measurement, and/or the jaw size and/or other relevant physical traits of the patient's mouth and/or the non-biological materials within the patient's mouth can be assessed. The arch-shaped body, set of arch-shaped bodies, or device that best corresponds to the patient can be selected to be worn by the patient during the MRI.

Patients undergoing an MRI can be from various ethnic backgrounds, and can have non-biological materials within their mouths (e.g., Ormco dental braces). These patients should not have contra-indications for receiving an MRI, such as a weak jaw or neck, certain metal implants in the craniofacial or neck regions, or female subjects who are pregnant or possibly pregnant. Patients who would require sedation before the MRI scan or who are unconscious may be fitted with an embodiment of the present external magnetic field correction devices or apparatuses like the one shown in FIGS. 9A and 9B.

Figure 9A:
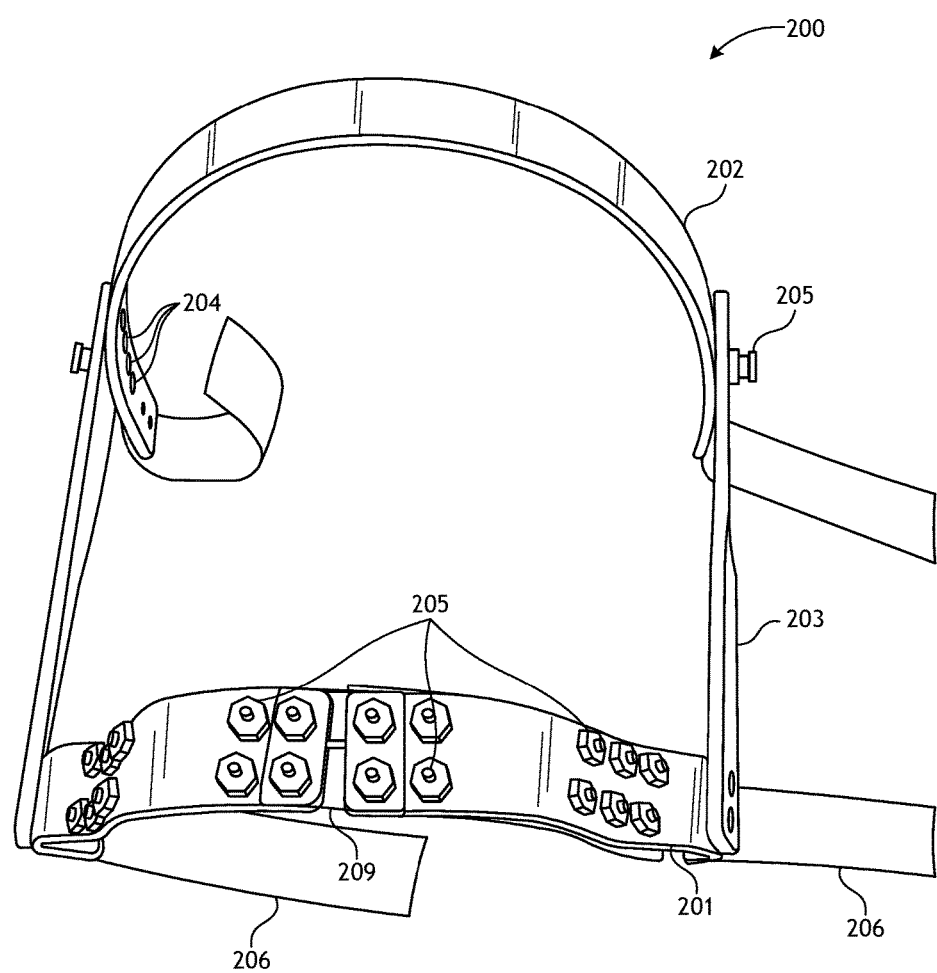
FIG. 9A is a perspective view of one embodiment of the present magnetic field correction devices configured to be worn outside of a user's mouth and coupled to a forehead support.

FIG. 9A depicts a perspective view of an embodiment of the present magnetic field correction devices and apparatuses 200 configured to be worn outside a user's mouth (e.g. an external embodiment). Device 200 comprises an arch-shaped body 201, which is contoured to fit over a user's face and may be located substantially over a user's mandible and maxilla, partially or substantially above a user's maxilla, or partially or substantially below a user's mandible. The depicted embodiment is configured such that, when located partially or substantially above or over a user's maxilla (or above or over the user's teeth), the arch-shaped body does not block or interfere with airflow through the user's mouth. Similarly, the present embodiments can be configured such that, when located partially or substantially below a user's mandible, the arch-shaped body does not block or interfere with airflow through the user's mouth or nose.

Figure 9B:
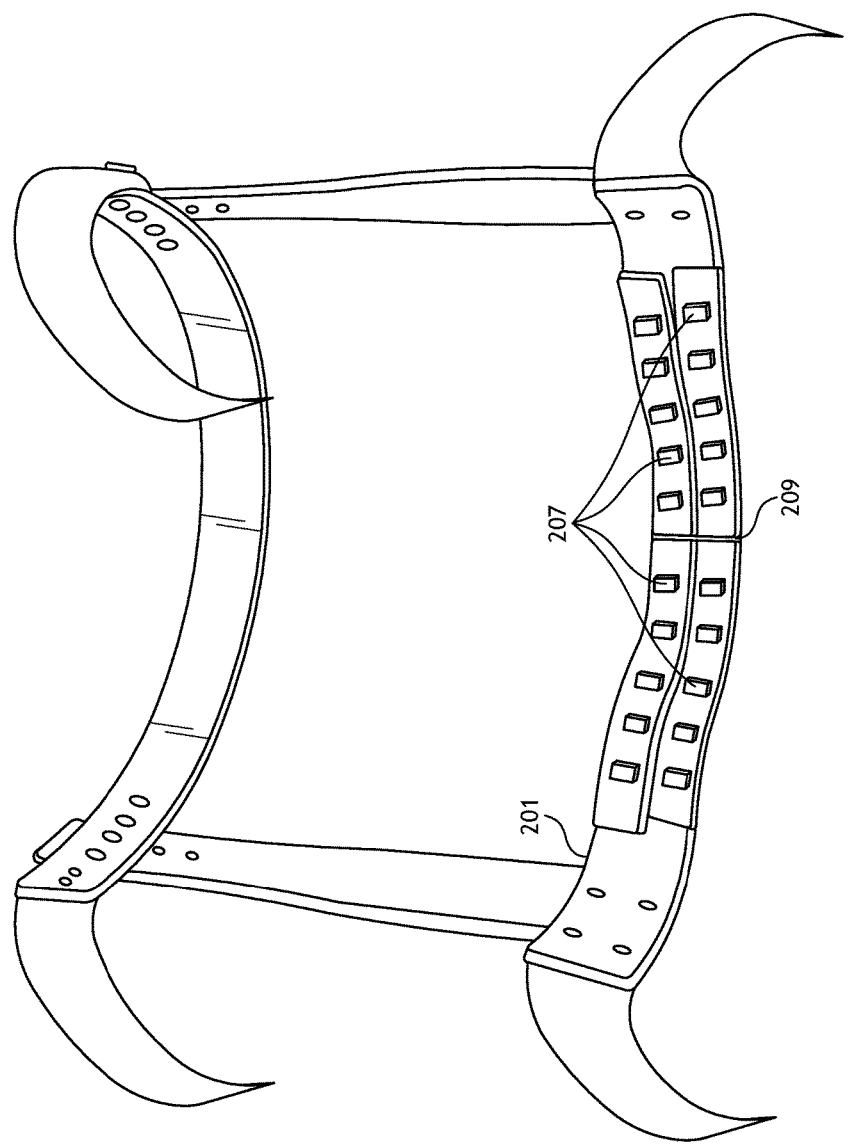
FIG. 9B is a second perspective view of the embodiment of FIG. 9A.

In the embodiment shown, arch-shaped body 201 is coupled to forehead support 202 via substantially rigid frame 203. Forehead support 202 is contoured to fit over the user's forehead and includes a plurality of openings 204 for coupling forehead support to frame 203 via a plurality of screw- and nut fasteners 205. The plurality of openings 204 permit frame 203 to couple with forehead support 202 at various locations to facilitate adjustment of frame 203 relative to the user's head. In this embodiment, screw-and-nut fasteners 205 are also employed to couple a plurality of members 207 comprising magnetically permeable material (shown in FIG. 9B) to arch-shaped body 201. Screw-and-nut fasteners 205 may be secured and removed by hand. In the depicted embodiment, device 200 further comprises straps 206, which are coupled to the ends of arch-shaped body 201 and forehead support 202, and are configured to secure arch-shaped body 201 and forehead support 202 to the user's head by wrapping around the back of the user's head and fastening to themselves by, for example, loop-and-fastener means. FIG. 9B depicts a perspective view of device 200 facing away from the user's face. As shown in FIG. 9B, arch-shaped body 201 is coupled to a plurality of members 207 comprising magnetically permeable material (e.g., permanent magnets). In some of the present external embodiments, such as the one shown in FIGS. 9A-9B, members 207 include strips (e.g., plastic strips) in which magnets are disposed or sealed, and the members 207 are in turn mounted on the arch shaped body outside the mouth. In the embodiment shown, these members (207) include four (4) members 207, one each for the user's left molars, left incisors, right incisors and right molars. In this embodiment, each strip can be mounted on the frame individually.

Device 200 or another external embodiment may also be used in conjunction or combination with an intraoral embodiment of the present devices and apparatuses to form a hybrid embodiment. Relative to an intraoral embodiment like that shown in FIG. 3A, an external embodiment of the present devices and apparatuses, like that shown in FIG. 9, permits greater freedom in the placement of magnets and other ferromagnetic materials to better compensate for variability of magnetic moments of orthodontic braces or other non-biological materials in a user's mouth. However, relative to external embodiments of the present devices and apparatuses, intraoral embodiments allow closer proximity between non-biological materials in a user's mouth and the magnets or other ferromagnetic materials of the devices or apparatuses. When used in combination, the advantages of both intraoral and external embodiments of the present devices and apparatuses can be utilized.

As shown in FIGS. 9A and 9B, in the depicted embodiment of device 209, arch-shaped body 210 includes a flexible (e.g., soft or otherwise pliable) link or joint 209 (e.g., at or near the lateral center of the body, as shown). In such embodiments, link or joint 209 is more flexible than other parts of arch-shaped body 201 (which may, for example, include rigid plastic) to allow body 201 (via link or joint 209) to flex to accommodate different maxillary (or mandibular) arch widths in patients.

Figure 11:
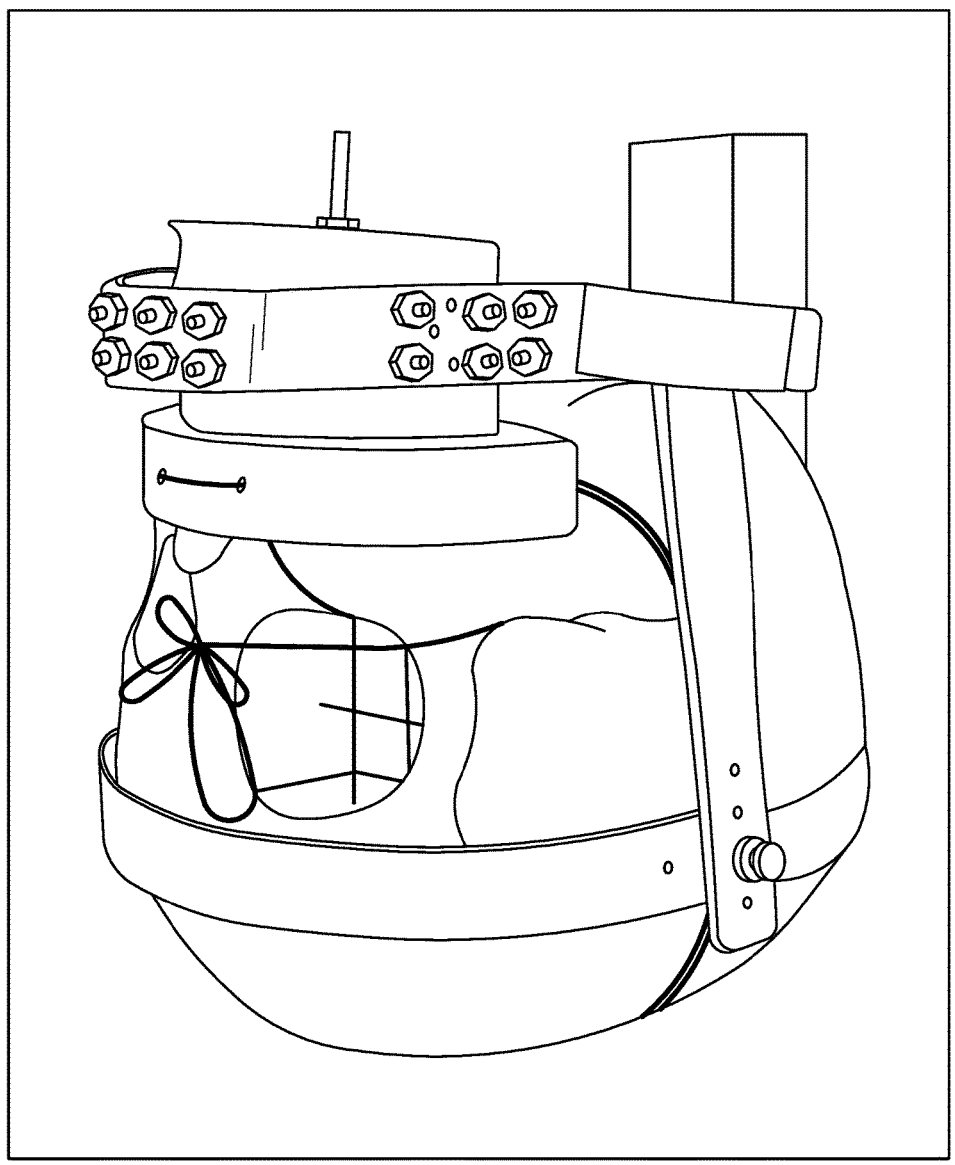
FIG. 11 is a perspective view the head phantom of FIG. 10 wearing an intraoral-external hybrid embodiment of the present magnetic field correction devices.

FIG. 11 depicts a hybrid external and intraoral embodiment of the present devices and apparatuses affixed to the head phantom shown in FIG. 10. As described previously, a head phantom such as that shown in FIGS. 10 and 11 in this application, simulates a patient with twenty-eight (28) stainless steel dental braces brackets mounted on twenty-eight (28) model teeth. The brain phantom was fitted with three different sized dental models (one of average size, one 8.5% bigger, and one 8.5% smaller) to investigate whether a one-size hybrid embodiment would sufficiently counter $B_0$ distortions in MRI images. The brain phantom shown in FIGS. 10 and 11 was filled with agar gel and evaluated for $B_0$ homogeneity in a similar manner shown and described above with reference to FIG. 7. In some such hybrid embodiments including intraoral and external components (which may be referred to as intraoral-external hybrid devices or systems), the intraoral component can be configured to mainly correct the magnetic field induced in incisor brackets (e.g., by including only or primarily magnets corresponding to the incisors), while the external component can be configured corrects both incisor and molar brackets (e.g., by including magnets corresponding to both the incisors and the molars).

The magnetic moments induced in orthodontic appliances are different for different vendors and models of orthodontic appliances. Molar brackets have a larger range of variability compared with incisor brackets. Embodiments of the present devices (and/or apparatuses and/or systems) can be included in or presented as a kit containing exchangeable components with different magnetic moments. In use for MRI examinations, an appropriate device and/or exchangeable components can be selected and assembled from such a kit based, for example, on a calibration $B_0$ scan and computer analysis of the scan to best match the braces that the patient is actually wearing. For example, embodiments of the present kits can include multiple maxillary and/or mandible pieces for an intraoral device, each of which pieces having different magnetic moments. Similarly, embodiments of the present kits can include multiple strips or members with embedded magnets of different magnetic moments for each mounting position on the frame. By using one particular maxillary piece and/or mandibular piece, a large range of possible total magnetic moments of braces can be matched.

Figure 12:
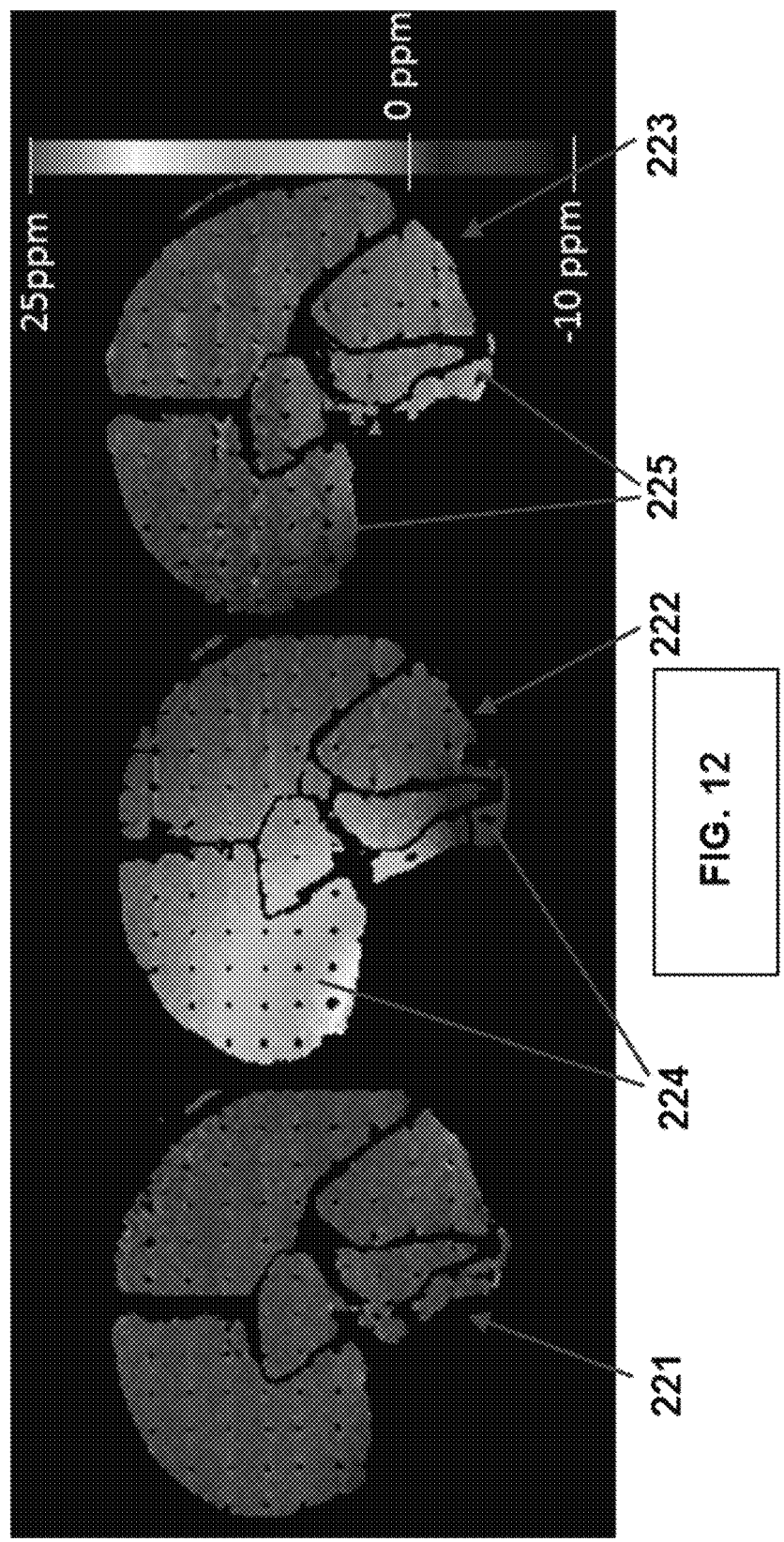
FIG. 12 depicts sagittal $\Delta B_0$ maps for a simulated patient without dental braces and without a magnetic field correction device, with dental braces and without a magnetic field correction device, and with dental braces and with a intraoral-external hybrid magnetic field correction device.

FIG. 12 shows the resulting sagittal $\Delta B_0$ maps. In particular, map 221 depicts the baseline results, i.e., when the brain phantom was not fitted with braces or an embodiment of the magnetic field correction device. Map 221 has a peak-to-peak $\Delta B_0$ value of 13.8 parts per million (ppm) and standard deviation of 0.40 ppm. Map 222 depicts $B_0$ homogeneity for the brain phantom when fitted with braces and without attaching any embodiment of the magnetic field correction device. Map 222 has a peak-to-peak $\Delta B_0$ value of between 28.7 and 32.2 parts per million (ppm), and standard deviation of between 3.0 and 3.1 ppm for the three dental model sizes. The relatively large peak-to-peak $\Delta B_0$ value (especially compared to that of map 221) is indicative of a loss of homogeneity in the MRI magnetic field due to the magnetic fields induced by the dental braces. Map 223 depicts $B_0$ homogeneity for the brain phantom when fitted with both braces and a hybrid embodiment of the magnetic field correction device. Map 223 shows reduced regions 225 of image distortion (e.g., compare map 223 with map 222). For map 223, the peak-to-peak $\Delta B_0$ value is 12.7 to 17.3 parts per million (ppm), with a standard deviation of 0.64 to 0.76 ppm. The significant reduction in peak-to-peak $\Delta B_0$ and from map 222 to map 223 is indicative of the magnetic field correction device partially restoring homogeneity to the MRI magnetic field; and is an even greater restoration than that shown in FIG. 7 when using only an intraoral magnetic field correction device. As shown in FIG. 12, a hybrid magnetic field correction devices can be configured to significantly improve $B_0$ homogeneity (e.g., by varying at least the number, strength, and/or positioning of magnets 62a and/or ferromagnetic materials 62b in both the intraoral and external features). The single-sized hybrid device was sufficient to adequately correct $B_0$ distortions.

In another related study, image quality with and without the braces, undergoing MRI scans for headaches/seizures in two of the patients, an optic nerve tumor in one of the patients, and a thalamic tumor in the last patient. The patients tolerated well the use of an external magnetic correction device and its use improved the quality of various MRI images, including orbital, sub-frontal, and anterior temporal MRIs, and, in particular, DWI.

Figures 13A, 13B:
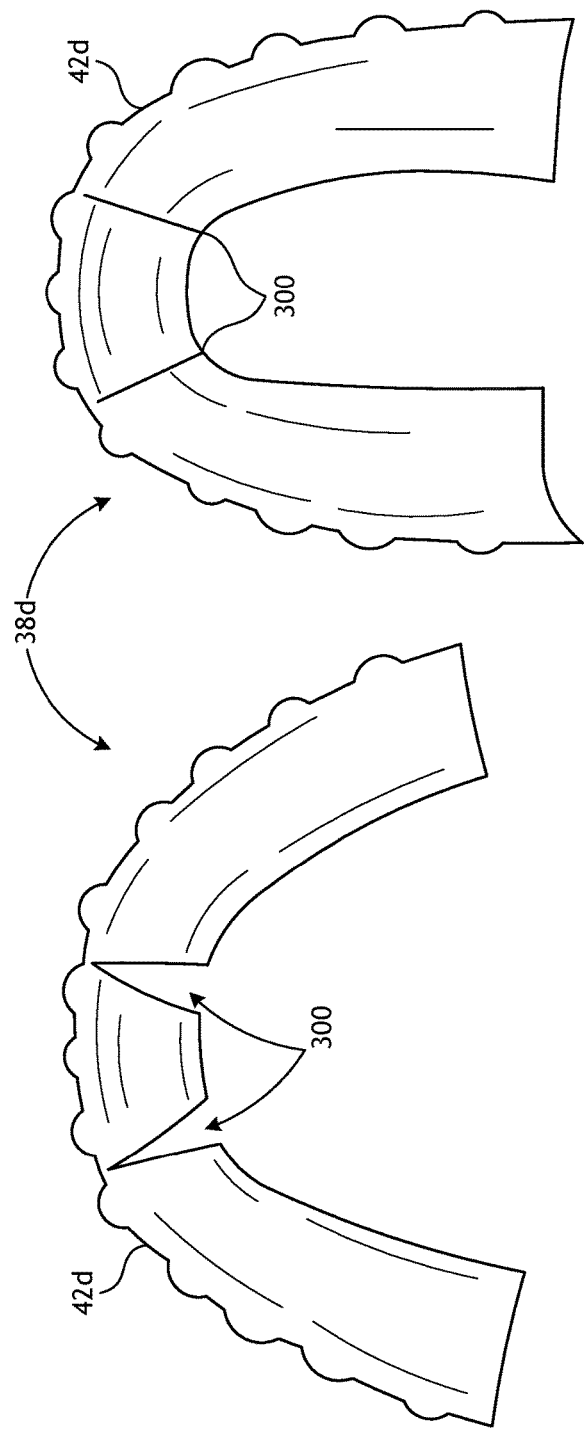
FIGS. 13A-13B depict another embodiment of the present intraoral devices.

FIGS. 13A-13B depict another embodiment 38d of the present intraoral devices. In this embodiment, arch-shaped body 42d includes two gaps or slits 300 to create flexible (e.g., soft or otherwise pliable) links or joints (e.g., at or near the lateral center of the body, as shown). In such embodiments, these gaps are more flexible than other parts of arch-shaped body 42d (which may, for example, include rigid plastic) to allow body 42d (via the gaps 300) to flex to accommodate different maxillary (or mandibular) arch widths in patients.

In some embodiment, the intraoral device is attached to a string that is configured to be tethered down around the neck of the patient as a safety measure. In case the device comes out of the patient's mouth, the string will prevent the device from moving away by the attraction force between the MRI magnet and the device. In some embodiments, the intraoral device is strengthened with extra coating using rubber or other materials to prevent to magnets from escaping or being released if the device breaks. The device may also be contained inside fabric pouch during use for the same purpose.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

These references, to the extent that they provide exemplary procedural or other details supplementary to those set forth herein, are specifically incorporated herein by reference.

1. New P F, Rosen B R, Brady T J, Buonanno F S, Kistler J P, Burt C T, Hinshaw W S, Newhouse J H, Pohost G M, and Taveras J M: Potential hazards and artifacts of ferromagnetic and nonferromagnetic surgical and dental materials and devices in nuclear magnetic resonance imaging. Radiology 1983; 147(1): p. 139-48. PMID: 6828719
2. Fache J S, Price C, Hawbolt E B, and Li D K: MR imaging artifacts produced by dental materials. AJNR Am J Neuroradiol 1987; 8(5): p. 837-40. PMID: 3118677.
3. Hinshaw D B, Jr., Holshouser B A, Engstrom H I, Tjan A H, Christiansen E L, and Catelli W F: Dental material artifacts on MR images. Radiology 1988; 166(3): p. 777-9. PMID: 3340777.
4. Shellock F G: Prosthetic heart valves and annuloplasty rings: assessment of magnetic field interactions, heating, and artifacts at 1.5 Tesla. J Cardiovasc Magn Reson 2001; 3(4): p. 317-24. PMID: 11777223.
5. Shellock F G: Metallic neurosurgical implants: evaluation of magnetic field interactions, heating, and artifacts at 1.5-Tesla. J Magn Reson Imaging 2001; 14(3): p. 295-9. PMID: 11536406.
6. Hashemi R H, Bradley W G, and Lisanti C J: MRI: The Basics. 3rd ed. 2010: Lippincott Williams & Wilkins.
7. Klinke T, Daboul A, Maron J, Gredes T, Puls R, Jaghsi A, and Biffar R: Artifacts in magnetic resonance imaging and computed tomography caused by dental materials. PLoS One 2012; 7(2): p. e31766. PMCID: PMC3285178.

8. Blankenstein F H, Truong B, Thomas A, Schroder R J, and Naumann M: Signal loss in magnetic resonance imaging caused by intraoral anchored dental magnetic materials. Rofo 2006; 178(8): p. 787-93. PMID: 16862505.
9. Bateman L M, Latchaw R, and Seyal M: Dental hardware complicating diagnosis in refractory gelastic epilepsy secondary to hypothalamic hamartoma. Clin EEG Neurosci 2010; 41(3): p. 151-4. PMID: 20722350.
10. Laakman R W, Kaufman B, Han J S, Nelson A D, Clampitt M, O'Block A M, Haaga J R, and Alfidi R J: MR imaging in patients with metallic implants. Radiology 1985; 157(3): p. 711-4. PMID: 4059558.
11. Shellock F G: MR imaging of metallic implants and materials: a compilation of the literature. AJR Am J Roentgenol 1988; 151(4): p. 811-4. PMID: 3048071.
12. Fellner C, Behr M, Fellner F, Held P, Handel G, and Feuerbach S: Artifacts in MR imaging of the temporomandibular joint caused by dental alloys: a phantom model study at T1.5. Rofo 1997; 166(5): p. 421-8. PMID: 9198515.
13. Saito M, Ono S, Kayanuma H, Honnami M, Muto M, and Une Y: Evaluation of the susceptibility artifacts and tissue injury caused by implanted microchips in dogs on 1.5 T magnetic resonance imaging. J Vet Med Sci 2010; 72(5): p. 575-81. PMID: 20086326.
14. Hargreaves B A, Worters P W, Pauly K B, Pauly J M, Koch K M, and Gold G E: Metal-induced artifacts in MRI. AJR Am J Roentgenol 2011; 197(3): p. 547-55. PMID: 21862795.
15. Buckwalter K A, Lin C, and Ford J M: Managing postoperative artifacts on computed tomography and magnetic resonance imaging. Semin Musculoskelet Radiol 2011; 15(4): p. 309-19. PMID: 21928156.
16. Hecht S, Adams W H, Narak J, and Thomas W B: Magnetic resonance imaging susceptibility artifacts due to metallic foreign bodies. Vet Radiol Ultrasound 2011; 52(4): p. 409-14. PMID: 21382122.
17. Bagheri M H, Hosseini M M, Emami M J, and Foroughi A A: Metallic artifact in MRI after removal of orthopedic implants. Eur J Radiol 2012; 81(3): p. 584-90. PMID: 21146947.
18. David F H, Grierson J, and Lamb C R: Effects of surgical implants on high-field magnetic resonance images of the normal canine stifle. Vet Radiol Ultrasound 2012; 53(3): p. 280-8. PMID: 22372640.
19. Mirvis S E, Geisler F, Joslyn J N, and Zrebeet H: Use of titanium wire in cervical spine fixation as a means to reduce MR artifacts. AJNR Am J Neuroradiol 1988; 9(6): p. 1229-31. PMID: 3143247.
20. Wichmann W, Von Ammon K, Fink U, Weik T, and Yasargil G M: Aneurysm clips made of titanium: magnetic characteristics and artifacts in MR. AJNR Am J Neuroradiol 1997; 18(5): p. 939-44. PMID: 9159374.
21. Rudisch A, Kremser C, Peer S, Kathrein A, Judmaier W, and Daniaux H: Metallic artifacts in magnetic resonance imaging of patients with spinal fusion. A comparison of implant materials and imaging sequences. Spine (Phila Pa. 1976) 1998; 23(6): p. 692-9. PMID: 9549791.
22. Immel E and Melzer A: Improvement of the MR imaging behavior of vascular implants. Minim Invasive Ther Allied Technol 2006; 15(2): p. 85-92. PMID: 16754191.
23. Ernstberger T, Buchhorn G, Baums M H, and Heidrich G: In-vitro MRI detectability of interbody test spacers made of carbon fibre-reinforced polymers, titanium and titanium-coated carbon fibre-reinforced polymers. Acta Orthop Belg 2007; 73(2): p. 244-9. PMID: 17515239.
24. Ernstberger T and Heidrich G: Postfusion magnetic resonance imaging artifacts caused by a titanium, cobalt-chromium-molybdenum, and carbon intervertebral disc spacer. J Spinal Disord Tech 2007; 20(2): p. 154-9. PMID: 17414986.
25. Ernstberger T, Heidrich G, Bruening T, Krefft S, Buchhorn G, and Klinger H M: The interobserver-validated relevance of intervertebral spacer materials in MRI artifacting. Eur Spine J 2007; 16(2): p. 179-85. PMCID: PMC2200688.
26. Ernstberger T, Heidrich G, and Buchhorn G: Postimplantation MRI with cylindric and cubic intervertebral test implants: evaluation of implant shape, material, and volume in MRI artifacting—an in vitro study. Spine J 2007; 7(3): p. 353-9. PMID: 17482121.
27. Ernstberger T, Heidrich G, Dullin C, Buchhorn G, and Grabbe E: Preclinical evaluation by flat-panel detector-based volumetric CT versus MRI of intervertebral spacers implanted in a porcine model. Spine J 2007; 7(3): p. 360-7. PMID: 17482122.
28. Ernstberger T, Heidrich G, Schultz W, and Grabbe E: Implant detectibility of intervertebral disc spacers in post fusion MRI: evaluation of the MRI scan quality by using a scoring system—an in vitro study. Neuroradiology 2007; 49(2): p. 103-9. PMID: 17086407.
29. Starcukova J, Starcuk Z, Jr., Hubalkova H, and Linetskiy I: Magnetic susceptibility and electrical conductivity of metallic dental materials and their impact on MR imaging artifacts. Dent Mater 2008; 24(6): p. 715-23. PMID: 17884157.
30. Ernstberger T, Buchhorn G, and Heidrich G: Artifacts in spine magnetic resonance imaging due to different intervertebral test spacers: an in vitro evaluation of magnesium versus titanium and carbon-fiber-reinforced polymers as biomaterials. Neuroradiology 2009; 51(8): p. 525-9. PMCID: PMC3085728.
31. Ernstberger T, Buchhorn G, and Heidrich G: Magnetic resonance imaging evaluation of intervertebral test spacers: an experimental comparison of magnesium versus titanium and carbon fiber reinforced polymers as biomaterials. Ir J Med Sci 2010; 179(1): p. 107-11. PMCID: PMC3128752.
32. Heyse T J, Chong le R, Davis J, Boettner F, Haas S B, and Potter H G: MRI analysis of the component-bone interface after TKA. Knee 2012; 19(4): p. 290-4. PMID: 21741843.
33. Pauchard Y, Smith M R, and Mintchev M P: Improving geometric accuracy in the presence of susceptibility difference artifacts produced by metallic implants in magnetic resonance imaging. IEEE Trans Med Imaging 2005; 24(10): p. 1387-99. PMID: 16229424.
34. Jin Z, Xia L, and Du Y P: Reduction of artifacts in susceptibility-weighted MR venography of the brain. J Magn Reson Imaging 2008; 28(2): p. 327-33. PMCID: PMC2782378.
35. Volz S, Hattingen E, Preibisch C, Gasser T, and Deichmann R: Reduction of susceptibility-induced signal losses in multi-gradient-echo images: application to improved visualization of the subthalamic nucleus. Neuroimage 2009; 45(4): p. 1135-43. PMID: 19349229.
36. Olsen R V, Munk P L, Lee M J, Janzen D L, MacKay A L, Xiang Q S, and Masri B: Metal artifact reduction sequence: early clinical applications. Radiographics 2000; 20(3): p. 699-712. PMID: 10835123.

37. Kolind S H, MacKay A L, Munk P L, and Xiang Q S: Quantitative evaluation of metal artifact reduction techniques. J Magn Reson Imaging 2004; 20(3): p. 487-95. PMID: 15332257.
38. Ramos-Cabrer P, van Duynhoven J P, Van der Toorn A, and Nicolay K: MRI of hip prostheses using single-point methods: in vitro studies towards the artifact-free imaging of individuals with metal implants. Magn Reson Imaging 2004; 22(8): p. 1097-103. PMID: 15527996.
39. Toms A P, Smith-Bateman C, Malcolm P N, Cahir J, and Graves M: Optimization of metal artefact reduction (MAR) sequences for MRI of total hip prostheses. Clin Radiol 2010; 65(6): p. 447-52. PMID: 20451011.
40. Koch K M, Brau A C, Chen W, Gold G E, Hargreaves B A, Koff M, McKinnon G C, Potter H G, and King K F: Imaging near metal with a MAVRIC-SEMAC hybrid. Magn Reson Med 2011; 65(1): p. 71-82. PMID: 20981709.
41. Sutter R, Ulbrich E J, Jellus V, Nittka M, and Pfirrmann C W: Reduction of metal artifacts in patients with total hip arthroplasty with slice-encoding metal artifact correction and view-angle tilting MR imaging. Radiology 2012; 265(1): p. 204-14. PMID: 22923720.
42. Lee Y H, Lim D, Kim E, Kim S, Song H T, and Suh J S: Usefulness of slice encoding for metal artifact correction (SEMAC) for reducing metallic artifacts in 3-T MRI. Magn Reson Imaging 2013; [Epub ahead of print]. PMID: 23290476.
43. Elison J M, Leggitt V L, Thomson M, Oyoyo U, and Wycliffe N D: Influence of common orthodontic appliances on the diagnostic quality of cranial magnetic resonance images. Am J Orthod Dentofacial Orthop 2008; 134(4): p. 563-72. PMID: 18929275.
44. Cox R J, Kau C H, and Rasche V: Three-dimensional ultrashort echo magnetic resonance imaging of orthodontic appliances in the natural dentition. Am J Orthod Dentofacial Orthop 2012; 142(4): p. 552-61. PMID: 22999679.
45. Cullity B D and Graham C D: Introduction to Magnetic Materials. 2nd ed. 2009: Wiley.
46. Wen Z, Fahrig R, Williams S T, and Pelc N J: Shimming with permanent magnets for the x-ray detector in a hybrid x-ray/MR system. Med Phys 2008; 35(9): p. 3895-902. PMCID: PMC2673662.
47. ACR: Phantom Test Guidance. Available from: http://www.acr.org/~/media/ACR/Documents/Accreditation/MRI/LargePhantomGuidance.pdf.
48. Phelan A, Petocz P, Walsh W, and Darendeliler M A: The force-distance properties of attracting magnetic attachments for tooth movement in combination with clear sequential aligners. Aust Orthod J 2012; 28(2): p. 159-69. PMID: 23304964.
49. TDK: Magnet Design Data. Available from: http://www.tdk.co.jp/magnet_e/e371.pdf.
50. Gholipour A, Kehtarnavaz N, Scherrer B, and Warfield S K: On the accuracy of unwarping techniques for the correction of susceptibility-induced geometric distortion in magnetic resonance Echo-planar images. Conf Proc IEEE Eng Med Biol Soc 2011; 2011: p. 6997-7000. PMID: 22255949.
51. Morelli J, Porter D, Ai F, Gerdes C, Saettele M, Feiweier T, Padua A, Dix J, Marra M, Rangaswamy R, and Runge V: Clinical evaluation of single-shot and readout-segmented diffusion-weighted imaging in stroke patients at 3 T. Acta Radiol 2013; [Epub ahead of print]. PMID: 23319722.
52. Adam C J, Askin G N, and Pearcy M J: Gravity-induced torque and intravertebral rotation in idiopathic scoliosis. Spine (Phila Pa. 1976) 2008; 33(2): p. E30-7. PMID: 18197088.
53. Palinkas M, Nassar M S, Cecilio F A, Siessere S, Semprini M, Machado-de-Sousa J P, Hallak J E, and Regalo S C: Age and gender influence on maximal bite force and masticatory muscles thickness. Arch Oral Biol 2010; 55(10): p. 797-802. PMID: 20667521.
54. Kagetsu N J and Litt A W: Important considerations in measurement of attractive force on metallic implants in MR imagers. Radiology 1991; 179(2): p. 505-8. PMID: 2014301.
55. Lopic N, Jelen A, Vrtnik S, Jaglicic Z, Wencka M, Starc R, Blinc A, and Dolinsek J: Quantitative determination of magnetic force on a coronary stent in MRI. J Magn Reson Imaging 2013; 37(2): p. 391-7. PMID: 23125054.
56. Bondemark L, Kurol J, and Wennberg A: Orthodontic rare earth magnets—in vitro assessment of cytotoxicity. Br J Orthod 1994; 21(4): p. 335-41. PMID: 7857892.
57. Donohue V E, McDonald F, and Evans R: In vitro cytotoxicity testing of neodymium-iron-boron magnets. J Appl Biomater 1995; 6(1): p. 69-74. PMID: 7703540.
58. Bondemark L: Orthodontic magnets. A study of force and field pattern, biocompatibility and clinical effects. Swed Dent J Suppl 1994; 99: p. 1-148. PMID: 7801229.
59. Boeckler A F, Morton D, Ehring C, and Setz J M: Mechanical properties of magnetic attachments for removable prostheses on teeth and implants. J Prosthodont 2008; 17(8): p. 608-15. PMID: 18761583.

The invention claimed is:

1. An apparatus comprising:
    an arch-shaped body configured to be worn outside of a user's mouth such that the arch-shaped body is configured to overlie a user's lips and follow a contour of at least some of the user's teeth;
    where the arch-shaped body comprises one or more sidewalls coupled to a plurality of members comprising magnetically permeable material such that the magnetically permeable material overlies a user's teeth when the apparatus is worn by a user.

2. The apparatus of claim 1, where the magnetically permeable material comprises one or more permanent magnets.

3. The apparatus of claim 2, where the one or more permanent magnets comprise a plurality of permanent magnets.

4. The apparatus of claim 1, further comprising one or more nut fasteners configured to couple the plurality of members to the one or more sidewalls.

5. An apparatus comprising:
    an arch-shaped body configured to be worn outside of a user's mouth such that the arch-shaped body overlies the user's teeth; and
    where the arch-shaped body comprises one or more sidewalls configured to be coupled to a plurality of members comprising magnetically permeable material.

6. The apparatus of claim 5, where:
    the arch-shaped body follows a contour of the user's face; and
    the magnetically permeable material comprises one or more permanent magnets.

7. The apparatus of claim 6, where the one or more permanent magnets comprise a plurality of permanent magnets.

8. The apparatus of claim 5, where:
the arch-shaped body does not obstruct an airway of the user when worn outside the user's mouth; and
the plurality of members are disposed on the arch-shaped body such that at least one of the plurality of members overlies each of the user's: left molars, left incisors, right incisors and right molars.

9. The apparatus of claim 7, where:
the plurality of members include strips in which the plurality of permanent magnets are sealed; and
the plurality of members are adjacent the user's maxilla and mandible.

10. The apparatus of claim 5, further comprising a forehead support, where the forehead support is configured such that it follows a contour of the user's forehead.

11. The apparatus of claim 10, where the forehead support comprises a plurality of openings.

12. The apparatus of claim 10, further comprising one or more frames connecting the arch-shaped body and the forehead support.

13. The apparatus of claim 12, where:
the arch-shaped body is substantially parallel to the forehead support; and
the one or more frames is substantially rigid.

14. The apparatus of claim 12 further comprising a plurality of nut- and screw fasteners.

15. The apparatus of claim 12, further comprising one or more straps coupled to the forehead support and configured to secure any of the following to the front of the user's head: the arch-shaped body, the forehead support, the one or more frames.

16. The apparatus of claim 5, where at least one of the one or more sidewalls comprises a curved surface, and the apparatus is configured to be worn by a user such that normal vectors along the surface lie substantially in a plane perpendicular to a magnetic field of a magnetic resonance imaging scanner.

17. The apparatus of claim 5, where at least some of the plurality of members comprise ferromagnetic material.

18. The apparatus of claim 5, further comprising a layer of material configured to be coupled to the at least one of the one or more sidewalls such that the layer of material overlies each of the plurality of members.

19. The apparatus of claim 5, where the plurality of members is configured to partially restore losses in magnetic field homogeneity caused by non-biological materials within the user's mouth during magnetic resonance imaging.

20. The apparatus of claim 5, where a total magnetic moment generated by the plurality of members is substantially equal but opposite to the magnetic moment induced by non-biological materials within the user's mouth during magnetic resonance imaging.

21. The apparatus of claim 19, where the non-biological materials within the user's mouth comprise dental braces.

22. An apparatus comprising:
an arch-shaped body configured to be worn outside a user's mouth such that the arch-shaped body follows a contour of the user's face with an upper portion of the arch-shaped body overlying maxillary teeth of the user and a lower portion of the arch-shaped body overlying mandibular teeth of the user when the user's mouth is closed;
where the arch-shaped body comprises one or more sidewalls configured to be coupled to a plurality of members comprising magnetically permeable material.

23. The apparatus of claim 22, where at least some of the plurality of members comprise ferromagnetic material.

24. The apparatus of claim 23, where the magnetically permeable material comprises one or more permanent magnets.

25. The apparatus of claim 24, where the one or more permanent magnets comprise a plurality of permanent magnets.

26. The apparatus of claim 23, where at least one of the one or more sidewalls of the arch-shaped body are configured to generate magnetic moments.

* * * * *

UNITED STATES PATENT AND TRADEMARK OFFICE
CERTIFICATE OF CORRECTION

PATENT NO. : 10,431,361 B2
APPLICATION NO. : 15/134211
DATED : October 1, 2019
INVENTOR(S) : Zhiyue J. Wang et al.

Page 1 of 1

It is certified that error appears in the above-identified patent and that said Letters Patent is hereby corrected as shown below:

In the Specification

Please add the following subheading and paragraph to Column 1 after Line 17:
STATEMENT OF GOVERNMENT SUPPORT
This invention was made with government support under grant number DE023917 awarded by The National Institutes of Health. The government has certain rights in the invention.

Signed and Sealed this
Ninth Day of June, 2020

Andrei Iancu
*Director of the United States Patent and Trademark Office*